US007875268B2

(12) United States Patent
Philippe et al.

(10) Patent No.: US 7,875,268 B2
(45) Date of Patent: Jan. 25, 2011

(54) DIMERCAPTOAMIDES, COMPOSITIONS COMPRISING THEM AS REDUCING AGENTS, AND PROCESSES FOR PERMANENTLY RESHAPING KERATIN FIBERS THEREWITH

(75) Inventors: Michel Philippe, Wissous (FR); Gérard Malle, Villiers S/Morin (FR); Christian Blaise, Saint Mande (FR)

(73) Assignee: L'Oreal S.A., Paris (FR)

( * ) Notice: Subject to any disclaimer, the term of this patent is extended or adjusted under 35 U.S.C. 154(b) by 1517 days.

(21) Appl. No.: 11/099,585

(22) Filed: Apr. 6, 2005

(65) Prior Publication Data

US 2006/0013784 A1   Jan. 19, 2006

Related U.S. Application Data

(60) Provisional application No. 60/562,229, filed on Apr. 15, 2004.

(30) Foreign Application Priority Data

Apr. 6, 2004   (FR)   ................................. 04 03598

(51) Int. Cl.
   *A61Q 5/04* (2006.01)
(52) U.S. Cl. .................. 424/70.2; 564/152; 564/154; 564/192; 564/193
(58) Field of Classification Search .................. None
   See application file for complete search history.

(56) References Cited

U.S. PATENT DOCUMENTS

| | | | |
|---|---|---|---|
| 4,137,420 | A | 1/1979 | Fujita et al. |
| 4,305,958 | A | 12/1981 | Fujita et al. |
| 4,366,827 | A | 1/1983 | Madrange et al. |
| 4,533,714 | A | 8/1985 | Sebag et al. |
| 4,587,321 | A | 5/1986 | Sebag et al. |
| 4,749,732 | A | 6/1988 | Kohl et al. |
| 4,880,618 | A | 11/1989 | Grollier et al. |
| 4,956,175 | A | 9/1990 | Maignan et al. |
| 4,996,059 | A | 2/1991 | Grollier et al. |
| 5,015,767 | A | 5/1991 | Maignan et al. |
| 5,085,860 | A | 2/1992 | Junino et al. |
| 5,106,612 | A | 4/1992 | Maignan et al. |
| 5,154,918 | A | 10/1992 | Maignan et al. |
| 5,214,181 | A | 5/1993 | Morita et al. |
| 5,334,377 | A | 8/1994 | Junino et al. |
| 5,350,572 | A | 9/1994 | Savaides et al. |
| 5,449,805 | A | 9/1995 | Junino et al. |
| 5,466,878 | A | 11/1995 | Junino et al. |
| 5,583,257 | A | 12/1996 | Junino et al. |
| 5,700,454 | A | 12/1997 | Malle |
| 5,843,416 | A | 12/1998 | Malle |
| 5,935,558 | A | 8/1999 | Malle |
| 5,958,392 | A | 9/1999 | Grollier et al. |
| 5,985,257 | A | 11/1999 | Malle |
| 2003/0064043 | A1 | 4/2003 | Dannecker et al. |
| 2003/0158184 | A1 | 8/2003 | Garvey et al. |

FOREIGN PATENT DOCUMENTS

| | | |
|---|---|---|
| DE | 10 95 805 B | 12/1960 |
| DE | 2 709 820 | 9/1977 |
| EP | 0 254 032 A2 | 1/1988 |
| EP | 0 295 780 A1 | 12/1988 |
| EP | 0 326 326 A1 | 8/1989 |
| EP | 0 354 835 | 2/1990 |
| EP | 0 432 000 | 6/1991 |
| EP | 0 465 342 | 1/1992 |
| EP | 0 514 282 | 11/1992 |
| EP | 0 653 202 | 5/1995 |
| FR | 2 470 596 | 6/1981 |
| FR | 2 472 382 | 7/1981 |
| FR | 2 495 931 | 6/1982 |
| FR | 2 535 730 | 5/1984 |
| FR | 2 598 613 | 11/1987 |
| GB | 2 197 352 A | 5/1988 |
| LU | 83703 | 6/1983 |
| WO | WO 91/08199 | 6/1991 |
| WO | WO 93/19024 | 9/1993 |
| WO | WO 97/30027 | 8/1997 |
| WO | WO 98/19672 | 5/1998 |
| WO | WO 01/74318 A2 | 10/2001 |
| WO | WO 02/39965 A2 | 5/2002 |

OTHER PUBLICATIONS

DE 1095805, Abstract (Dec. 1960).*
English language Derwent Abstract for FR 1 530 369.
English language Derwent Abstract for FR 2 514 640.
English language Derwent Abstract for EP 03 68 763.
English language Derwent Abstract for JP 3-176466.
English language Derwent Abstract for FR 2 679 448.
English language Derwent Abstract for FR 2 692 481.
English language Derwent Abstract for JP 08-157448.
English language Derwent Abstract for EP 07 21 772.
French Search Report for FR 0403598, Nov. 23, 2004.
Moynihan et al., "Preparation of Some Novel S-Nitroso Compounds as Potential Slow-Release Agents of Nitric Oxide in vivo," J. Chem. Soc. Perkin Trans. 1(7), 1994, 797-806.
"New Sulfhydryl Compounds with Potent Antihypertensive Activities," Chem. Pharm. Bull., 26(4), 1333-1335 (1978).

(Continued)

*Primary Examiner*—Jyothsna A Venkat
(74) *Attorney, Agent, or Firm*—Finnegan, Henderson, Farabow, Garrett & Dunner, LLP

(57) ABSTRACT

The present disclosure relates to specific dimercaptoamides, reducing compositions for permanently reshaping keratin fibers comprising the dimercaptoamides, for instance, human keratin fibers such as the hair; and processes for reshaping keratin fibers comprising the application of said reducing compositions. The present disclosure also relates to processes for preparing the dimercaptoamides.

14 Claims, No Drawings

OTHER PUBLICATIONS

Mita Ito et al., "Synthesis and Pharmacological Activities of Novel Cyclic Disulfide and Cyclic Sulfide Derivatives as Hepatoprotective Agents," Chem. Pharm. Bull., 41(6), 1066-1073 (1993).

Oya et al., "Thiol Compounds II Sythesis and Antihypertensive Activity of Mercaptoacylamino Acids," Chem. Pharm. Bull., 29(4), 940-947 (1981).

Cynkier et al., "Regiospecific Dimerization Leading to a 14-Membered Heterocyclic Ring, Synthesis and X-ray Structure," J. Org. Chem., 44(25), 4699-4701 (1979).

Rosenau et al., "A Vitamin E Derivative as a Novel, Extremely Advantageous Amino-Protecting Group," J. Org. Chem., 60(25), 8120-8121 (1995).

Bondi et al., "On The Synthesis of Glutathione In Human Blood Cells In Vitro," Israel Journal of Chemistry, vol. 11, No. 4, pp. 573-586 (1973).

Herter, "The Journal of Biological Chemistry", vol. 118, p. 327 (1937).

Herter, "The Journal of Biological Chemistry", vol. 121, p. 12 (1937).

Capasso et al., "A Study of the Aerial Oxidation of I-Cysteinyl-L-cysteine: Purification of the Product and Equilibrium Relationship involving the Monomeric and Dimeric Cyclic Derivatives," J. chem. Soc. Perkin Trans. 2, 1297-1300 (1980).

Hooper et al., "Polypeptides. Part II, The Preparation of Some Protected Peptides of Cysteine and Glycine," J. Chem. Soc., 3148-3151 (1956).

Guillaumie et al., "Immobilization of Pectin Fragments on Solid Supports: Novel Coupling by Thiazolidine Formation", Biconjugate Chemistry 2002, 13(2), 285-294.

Huang et al., "Synthesis and Electrochemistry of $Mo[BH(Me_2pz)_3](NO)[S(CH_2)_2CONH(CH_2)_2S]$ as a Probe of the Effects of N-H-S Hydrogen Bonding on Redox Potentials," Inorganic Chemstry 1995, 34(5), 1090-93.

Morishima et al., "Tableting Properties of Bucillamine Agglomerates Prepared by the Spherical Crystallization Technique," International Journal of Pharmaceutics, 105(1), 11-18 (1994).

Chem. & Pharm. Bulletin 1981, 29 (4), 940-7 (see p. 6 of spec.).

Panossian et al., "Zinc (II) and Nickel (II) Complexes of Cysteinyl-Cysteine," Spectroscopy Letters, 16(6), 463-70 (1983).

Gronowitz et al., "Conformational Effects on Disulfide Formation from Unsymmetrical Dithiols", Chemica Scripta, vol. 16, No. 3 (1980).

J. Huang et al., "Inorganic Chemistry", vol. 34, No. 5, 1995, pp. 1090-1093, XP-002307033, p. 1091, col. 1, lines 9-20.

Database Caplus Chemical Abstracts Service, Columbus, Ohio, US XP002307149, Database accession No. 1991: 679408, Santen Pharmaceutical Co. Ltd., Jul. 31, 1991.

Database Caplus Chemical Abstracts Service, Columbus, Ohio, US: XP002307151, Database accession No. 1996:545085, Jun. 18, 1996.

* cited by examiner

DIMERCAPTOAMIDES, COMPOSITIONS COMPRISING THEM AS REDUCING AGENTS, AND PROCESSES FOR PERMANENTLY RESHAPING KERATIN FIBERS THEREWITH

This application claims benefit of U.S. Provisional Application No. 60/562,229, filed Apr. 15, 2004, and French Application No. 04/03598 filed Apr. 6, 2004, the contents of both of which are incorporated herein by rereference.

The present disclosure relates to the use of dimercaptoamides as reducing agents for permanently reshaping keratin fibers, for instance, human keratin fibers such as the hair. It also relates to a process for permanently reshaping keratin fibers using said dimercaptoamides, and also to the process for preparing the novel dimercaptoamides and to the compositions comprising them.

The most common technique for obtaining permanent reshaping of the hair comprises, first, opening the disulphide bonds of the keratin (or cystine) by means of a composition containing a reducing agent, and then, for example, after having optionally rinsed the hair, in reconstituting the disulphide bonds by applying to the hair, which has been placed under tension beforehand with curlers or the like or shaped or smoothed out by other means, an oxidizing composition also known as a fixing composition, so as to give the hair the desired shape. This technique can make it possible, without distinction, either to make the hair wavy or to relax it, straighten it or smooth it out.

The reducing compositions generally used for the first step of a permanent-waving operation may contain sulphites, bisulphites or frequently thiols as the reducing agent. Among the thiols, those commonly used are thioglycolic acid, cysteamine, thiolactic acid, cysteine and glyceryl monothioglycolate. For example, thioglycolic acid is efficient at reducing the disulphide bonds of keratin at alkaline pH, such as in the form of ammonium thioglycolate, and is the product most commonly used in permanent-waving. However, it has been found that thioglycolic acid must be used in a sufficiently basic medium (in practice at a pH≧8.5) if it is desired to obtain curling of sufficient intensity. In addition to the drawback of releasing an unpleasant odor requiring the use of more or less efficient fragrances to mask the odors, the combination of thioglycolic acid and an alkaline pH leads can lead to degradation of the hair fiber.

Sulphites or bisulphites were used prior to thiols in general and to thioglycolic acid specifically. Unlike thiols, they are used at an acidic pH, generally ranging from pH 4 to pH 6. However, the degree of curling obtained may be much less and far from being satisfactory.

Cysteine produces a much weaker odor than that of thioglycolic acid, but the degree of curling obtained can also be much less and far from being satisfactory. In addition, cysteine requires the use of a very alkaline pH.

Glyceryl monothioglycolate also has a very strong unpleasant smell. It is, on the other hand, used at a pH close to neutral, but its performance levels can be notably inferior to those of thioglycolic acid.

Cysteamine can be used over a broader pH range. Its effectiveness is similar to that of thioglycolic acid, but it can also lead to considerable degradation of the hair fiber.

Much research has been carried out with a view to remedying the drawbacks of these reducing agents and, to this effect, the use of new reducing compounds or systems has been proposed. However, very few dithiols have been proposed. In the past, two specific dithiols had been widely studied: dithiothreitol DTT, and 2,5-dimercaptoadipic acid, but they have never been developed for permanently reshaping the hair, because for example, of the very unpleasant odour for DTT and the insufficient activity for dimercaptoadipic acid. More recently, in European Patent Application No. EP-A-0 721 772, the use of 2,3-dimercaptosuccinic acid was proposed, but this has proved to be less effective than thioglycolic acid. The use of polyoxyethyleneglycol dimercaptoalkyl esters has also been proposed in U.S. Pat. No. 5,350,572. Although these compounds may have a certain level of effectiveness, their storage over time can be unsatisfactory.

The present inventors have now discovered, surprisingly, that the use of certain dimercaptoamides as reducing agents can result in curling that can be satisfactory both in terms of intensity and in terms of hold over time, and can also result in a less substantial degradation of the fiber compared with the reducing agents of the prior art previously mentioned.

Accordingly, one aspect of the present disclosure is the use, as a novel reducing agent for permanently reshaping keratin fibers, for instance human keratin fibers such as the hair, of a dimercaptoamide of formula (I) and the organic and inorganic salts thereof:

$$\text{HS-A-CO-NH-B-SH} \qquad (I)$$

wherein:

A is chosen from $(CH_2)_n$ radicals, with n being an integer ranging from 1 to 5, optionally substituted with:

(i) linear or branched $C_1$-$C_5$ alkyl radicals; phenyl; benzyl; amino; acetylamino; NH—CO—CH$_2$—NH$_2$; NH—CO—CH$_2$—CH$_2$—CH(NH$_2$)COOH; NH—CO—CH$_2$—CH$_2$—CH(COOH)COOH; CH$_2$—COOH; CH$_2$—COOCH$_3$; or CH$_2$—COOCH$_2$—CH$_3$ radicals, or (ii) two methyl radicals or two ethyl radicals, and B is chosen from $(CH_2)_p$ radicals, with p being an integer ranging from 1 to 5, optionally substituted with:

(i) linear or branched $C_1$-$C_5$ alkyl radicals; carboxyl; COOCH$_3$; COOEt; CONH$_2$; CONH—CH$_3$; CON(CH$_3$)$_2$; CONH—CH$_2$—CH$_3$; CON(CH$_2$—CH$_3$)$_2$; CONH—CH$_2$—CHOH—CH$_3$; CO—NH—CH(COOH)—(CH$_2$)$_4$—NH$_2$; CO—NH—CH(COOH)—(CH$_2$)$_4$—N(CH$_3$)$_2$; CO—NH—CH$_2$—CH$_2$—COOEt; CO—NH—CH(COOH)-iPr; or CO—NH—CH$_2$—R radicals, wherein R is chosen from CO—NH$_2$, (CH$_2$)$_3$—NH$_2$, (CH$_2$)$_4$—NH$_2$, (CH$_2$)$_5$—NH$_2$, or (CH$_2$)$_4$—OH radicals, or (ii) 2 methyl radicals, wherein the sum of n+p ranges from 2 to 6.

Among the inorganic salts that may be used, non-limiting mention may be made of the salts of inorganic acids, such as sulphuric acid, hydrochloric acid, hydrobromic acid, hydriodic acid, phosphoric acid or boric acid. Non-limiting mention may also be made of the salts of organic acids, which may comprise at least one group chosen from carboxylic acid, sulphonic acid and phosphonic acid groups. They may be linear, branched or cyclic aliphatic acids or alternatively aromatic acids. These acids may also comprise at least one heteroatom chosen from O and N, for example in the form of hydroxyl groups. Non-limiting mention may also be made of propionic acid, acetic aid, terephthalic acid, citric acid and tartaric acid.

The neutralization of the anionic groups can be carried out with an inorganic base, such as LiOH, NaOH, KOH, Ca(OH)$_2$, NH$_4$OH, Mg(OH)$_2$ or Zn(OH)$_2$; or with an organic base such as a primary, secondary or tertiary alkylamine, for instance, triethylamine or butylamine. This primary, secondary or tertiary alkylamine may comprise at least one nitrogen and/or oxygen atom and may therefore comprise, for example, at least one alcohol functional groups; non-limiting mention may also be made of 2-amino-2-methylpropanol, triethanolamine and dimethylamino-2-propanol. Further non-limiting mention may also be made of lysine or 3-(dimethylamino)propylamine.

Another aspect of the present disclosure is a process for permanently reshaping keratin fibers, for example, human keratin fibers such as the hair, comprising applying to the keratin fibers a reducing composition comprising at least one compound of formula (I).

Still another aspect of the present disclosure is an aqueous reducing composition for permanently reshaping the hair, comprising, as reducing agent, a dimercaptoamide of formula (I). Finally, the present disclosure relates to novel dimercaptoamides.

Other characteristics, aspects, subjects and benefits of the present disclosure will emerge even more clearly upon reading the description and the examples which follow.

As used herein, the term "permanently reshaping keratin fibers" is understood to mean the permanent curling (also called permanent-waving), the relaxing or the straightening of keratin fibers.

The compounds of formula (I) can be prepared according to the procedures described in the following references:
J. Chem. Soc. PERKIN Trans. 1, (7), 1994, 797-806;
Chem. Pharm. Bull., 26, 1978, 1333-1335;
Chem. Pharm. Bull., 41(6), 1993, 1066-1073;
Chem. Pharm. Bull., 29(4), 1981, 940-947;
Santen DE 2709820;
J. Org. Chem., 44(25), 1979, 4699-4701;
J. Org. Chem., 60(25), 1995, 8120-8121;
Isr. J. Chem., 11, 1973, 573-586;
J. Biol. Chem., 118, 1937, 327;
J. Biol. Chem., 121, 1937, 12;
J. Chem. Soc. PERKIN Trans. 2, 1980, 1297-1300;
J. Chem. Soc., 1956, 3148-3151;
U.S. Publication No. 2003/158184 A1;
Bioconjugate Chemistry 2002, 13(2), 285-294;
PCT Application No. WO 9819672 A1;
PCT Application No. WO 9730027 A1;
Inorganic Chemistry 1995, 34(5), 1090-3;
International Journal of Pharmaceutics 1994, 105(1), 11-18;
PCT Application No. WO 9319024 A3;
PCT Application No. WO 9108199 A1;
European Patent No. EP 326 326 B1;
European Patent Application No. EP 254 032 A3;
Spectroscopy Letters 1983, 16(6), 463-70;
Chemical & Pharmaceutical Bulletin 1981, 29(4), 940-7;
Chemica Scripta 1980, 16(3), 97-101; and
U.S. Pat. No. 4,305,958.

Among the reducing agents of formula (I) that may be used according to the present disclosure, non-limiting mention may be made of, for example:
2-mercapto-N-(mercaptomethyl)acetamide,
2-mercapto-N-(2-mercaptoethyl)acetamide,
2-mercapto-N-(3-mercaptopropyl)acetamide,
2-mercapto-N-(4-mercaptobutyl)acetamide,
2-mercapto-N-(5-mercaptopentyl)acetamide,
3-mercapto-2-(2-mercaptoacetylamino)propionamide,
3-mercapto-2-(2-mercaptoacetylamino)-N,N-dimethylpropionamide,
2-mercapto-N-(2-mercapto-1,1-dimethylethyl)acetamide,
2-mercapto-N-(1-mercaptomethylpropyl)acetamide,
ethyl mercapto[(mercaptoacetyl)amino]acetate,
N-(mercaptoacetyl)-L-cysteine,
N-(mercaptoacetyl)-L-homocysteine,
N-(mercaptoacetyl)-L-homocysteine, sodium salt,
2-mercapto-N-mercaptomethylpropionamide,
2-mercapto-N-(2-mercaptoethyl)propionamide,
2-mercapto-N-(3-mercaptopropyl)propionamide,
2-mercapto-N-(4-mercaptobutyl)propionamide,
2-mercapto-N-(5-mercaptopentyl)propionamide,
mercapto-[(2-mercapto-1-oxopropyl)amino]acetic acid,
N-(2-mercapto-1-oxopropyl)-DL-cysteine,
(R)-N-(2-mercapto-1-oxopropyl)-L-cysteine,
(S)-N-(2-mercapto-1-oxopropyl)-L-cysteine,
2-mercaptopropionyl-L-cysteine,
N-(1-carbamoyl-2-mercaptoethyl)-2-mercaptopropionamide,
N-(1-dimethylcarbamoyl-2-mercaptoethyl)-2-mercaptopropionamide,
4-mercapto-2-(2-mercaptopropionylamino)butyric acid,
2-mercapto-N-(2-mercapto-1,1-dimethylethyl)propionamide
2-mercaptobutanoic acid mercaptomethylamide,
2-mercaptobutanoic acid (2-mercaptoethyl)amide,
2-mercaptobutanoic acid (3-mercaptopropyl)amide,
2-mercaptobutanoic acid (4-mercaptobutyl)amide,
2-mercaptobutanoic acid (5-mercaptopentyl)amide,
2-mercaptobutanoic acid (1-carbamoyl-2-mercaptoethyl)amide,
N-(1-dimethylcarbamoyl-2-mercaptoethyl)-2-mercaptobutyramide,
2-mercaptobutanoic acid (1-carbamoyl-3-mercaptopropyl)amide,
2-mercaptobutanoic acid (2-mercapto-1,1-dimethylethyl)amide,
2-mercaptopentanoic acid mercaptomethylamide,
2-mercaptopentanoic acid (2-mercaptoethyl)amide,
2-mercaptopentanoic acid (3-mercaptopropyl)amide,
2-mercaptopentanoic acid (4-mercaptobutyl)amide,
2-mercaptopentanoic acid (5-mercaptopentyl)amide,
3-mercapto-2-(2-mercaptopentanoylamino)propionic acid,
2-mercaptopentanoic acid (1-carbamoyl-2-mercaptoethyl)amide,
2-mercaptopentanoic acid (1-dimethylcarbamoyl-2-mercaptoethyl)amide,
2-mercaptopentanoic acid (1-carbamoyl-3-mercaptopropyl)amide,
2-mercaptopentanoic acid (2-mercapto-1,1-dimethylethyl)amide,
ethyl mercapto[(mercaptophenylacetyl)amino]acetate,
(R)-N-[2-(mercaptomethyl)-1-oxo-3-phenylpropyl]-L-cysteine,
(R)-N-[2-(mercaptomethyl)-1-oxo-3-phenylpropyl]-L-homocysteine,
(S)-N-[2-(mercaptomethyl)-1-oxo-3-phenylpropyl]-L-homocysteine,
3-mercapto-N-(2-mercaptoethyl)propanamide,
3-mercapto-N-mercaptomethylpropionamide,
3-mercapto-N-(3-mercaptopropyl)propionamide,
3-mercapto-N-(4-mercaptobutyl)propionamide,
N-(3-mercapto-1-oxopropyl)-L-cysteine,
3-mercapto-2-(3-mercaptopropionylamino)propionamide,
N-(1-dimethylcarbamoyl-2-mercaptoethyl)-3-mercaptopropionamide,
4-mercapto-2-(3-mercaptopropionylamino)butyric acid,
3-mercapto-N-(2-mercapto-1,1-dimethylethyl)propionamide,
3-mercapto-N-mercaptomethyl-2-methylpropionamide,
3-mercapto-N-(2-mercaptoethyl)-2-methylpropionamide,
3-mercapto-N-(3-mercaptopropyl)-2-methylpropionamide,
3-mercapto-N-(4-mercaptobutyl)-2-methylpropionamide, 3-mercapto-2-(3-mercapto-2-methylpropionylamino)propionic acid,
N-(1-carbamoyl-2-mercaptoethyl)-3-mercapto-2-methylpropionamide,
N-(1-dimethylcarbamoyl-2-mercaptoethyl)-3-mercapto-2-methylpropionamide,
3-mercapto-N-(2-mercapto-1,1-dimethylethyl)-2-methylpropionamide,
N-(3-mercapto-2-methyl-1-oxopropyl)-L-homocysteine,
N-[2-(mercaptomethyl)-1-oxo-3-phenylpropyl]cysteine,
methyl 4-[(1-carboxy-2-mercaptoethyl)amino]-3-(mercaptomethyl)-4-oxobutanoate,
N-mercaptomethyl-3-mercaptomethylsuccinamic acid,
N-(2-mercaptoethyl)-3-mercaptomethylsuccinamic acid,
N-(3-mercaptopropyl)-3-mercaptomethylsuccinamic acid,
N-(4-mercaptobutyl)-3-mercaptomethylsuccinamic acid,
N-(1-carboxy-2-mercaptoethyl)-3-mercaptomethylsuccinamic acid,
N-(1-carboxy-3-mercaptopropyl)-3-mercaptomethylsuccinamic acid,
N-(2-mercapto-1,1-dimethylethyl)-3-mercaptomethylsuccinamic acid,
N-(2-mercapto-1-ethyl)-3-mercaptomethylsuccinamic acid,
2-mercapto-N-mercaptomethyl-2-methylpropionamide,
2-mercapto-N-(2-mercaptoethyl)-2-methylpropanamide,
2-mercapto-N-(3-mercaptopropyl)-2-methylpropionamide,
2-mercapto-N-(4-mercaptobutyl)-2-methylpropionamide,
2-mercapto-N-(5-mercaptopentyl)-2-methylpropionamide,
2-mercapto-N-(2-mercapto-1,1-dimethylethyl)-2-methylpropionamide,
2-mercapto-N-(2-mercapto-1-ethyl)-2-methylpropionamide,
N-(2-mercapto-2-methyl-1-oxopropyl)-D-cysteine,
N-(2-mercapto-2-methyl-1-oxopropyl)cysteine,
N-(2-mercapto-2-methyl-1-oxopropyl)-L-cysteine, monosodium salt,
N-(2-mercapto-2-methyl-1-oxopropyl)-L-cysteine,
(R)-N-[2-amino-1-(mercaptomethyl)-2-oxoethyl]-2-mercapto-2-methylpropanamide,
methyl N-(2-mercapto-2-methyl-1-oxopropyl)-L-cysteinate,
(2R)-3-mercapto-2-[(2-mercapto-2-methyl-1-oxopropyl)amino]-N,N-dimethylpropanamide,
N2-[N-(2-mercapto-2-methyl-1-oxopropyl)-L-cysteinyl]-L-lysine,
N-(2-mercapto-2-methyl-1-oxopropyl)homocysteine,
N-(2-ethyl-2-mercapto-1-oxobutyl)-L-cysteine,
3-mercapto-N-mercaptomethyl-3-methylbutyramide,
3-mercapto-N-(2-mercaptoethyl)-3-methylbutanamide,
3-mercapto-N-(3-mercaptopropyl)-3-methylbutyramide,
3-mercapto-N-(4-mercaptobutyl)-3-methylbutyramide,
N-(3-mercapto-3-methyl-1-oxobutyl)-L-cysteine,
N-(1-carbamoyl-2-mercaptoethyl)-3-mercapto-3-methylbutyramide,
N-(1-dimethylcarbamoyl-2-mercaptoethyl)-3-mercapto-3-methylbutyramide,
4-mercapto-2-(3-mercapto-3-methylbutyrylamino)butyric acid,
3-mercapto-N-(2-mercapto-1,1-dimethylethyl)-3-methylbutyramide,
3-mercapto-N-(2-mercapto-1-ethyl)-3-methylbutyramide,
3-mercapto-N-mercaptomethyl-2,2-dimethylpropionamide,
3-mercapto-N-(2-mercaptoethyl)-2,2-dimethylpropionamide,
3-mercapto-N-(3-mercaptopropyl)-2,2-dimethylpropionamide,
3-mercapto-N-(4-mercaptobutyl)-2,2-dimethylpropionamide,
3-mercapto-N-(2-mercapto-1,1-dimethylethyl)-2,2-dimethylpropionamide,
N-(3-mercapto-2,2-dimethyl-1-oxopropyl)-D-cysteine,
N-(3-mercapto-2,2-dimethyl-1-oxopropyl)-L-cysteine,
N-(1-carbamoyl-2-mercaptoethyl)-3-mercapto-2,2-dimethylpropionamide,
N-(1-dimethylcarbamoyl-2-mercaptoethyl)-3-mercapto-2,2-dimethylpropionamide,
N-(3-mercapto-2,2-dimethyl-1-oxopropyl)-D-cysteinylglycinamide,
N6-[(1,1-dimethylethoxy)carbonyl]-N2-[N-(3-mercapto-2,2-dimethyl-1-oxopropyl)-L-cysteinyl]-L-lysine,
N-[2-[(4-aminobutyl)amino]-1-(mercaptomethyl)-2-oxoethyl]-3-mercapto-2,2-dimethylpropanamide, monohydrochloride,
N-[2-[(5-aminopentyl)amino]-1-(mercaptomethyl)-2-oxoethyl]-3-mercapto-2,2-dimethylpropanamide, monohydrochloride,
N-[2-[(6-aminohexyl)amino]-1-(mercaptomethyl)-2-oxoethyl]-3-mercapto-2,2-dimethylpropanamide, monohydrochloride,
(R)-N-[2-[(5-hydroxypentyl)amino]-1-(mercaptomethyl)-2-oxoethyl]-3-mercapto-2,2-dimethylpropanamide,
N2-[N-(3-mercapto-2,2-dimethyl-1-oxopropyl)-L-cysteinyl]-L-lysine,
N2-[N-(3-mercapto-2,2-dimethyl-1-oxopropyl)-L-cysteinyl]-N6,N6-dimethyl-L-lysine,
3-mercapto-N-(3-mercapto-2,2-dimethyl-1-oxopropyl)-D-valine,
N-(3-mercapto-2,2-dimethyl-1-oxopropyl)homocysteine
N-[2-ethyl-2-(mercaptomethyl)-1-oxobutyl]-L-cysteine,
2-amino-3-mercapto-N-mercaptomethylpropionamide,
(2R)-2-amino-3-mercapto-N-(2-mercaptoethyl)propanamide,
(2S)-2-amino-3-mercapto-N-(2-mercaptoethyl)propanamide,
2-amino-3-mercapto-N-(3-mercaptopropyl)propionamide,
2-amino-3-mercapto-N-(4-mercaptobutyl)propionamide,
L-cysteinyl-L-cysteine,
methyl mercapto[(mercaptoacetyl)amino]acetate,
ethyl L-cysteinyl-L-cysteinate,
2-amino-N-(1-carbamoyl-2-mercaptoethyl)-3-mercaptopropionamide,
2-amino-N-(1-carbamoyl-2-mercaptoethyl)-3-mercapto-N,N-dimethylpropionamide,
2-(2-amino-3-mercaptopropionylamino)-4-mercaptobutyric acid,
2-amino-3-mercapto-N-(2-mercapto-1,1-dimethylethyl)propionamide,
2-amino-3-mercapto-N-(2-mercapto-1-ethyl)propionamide,
2-acetylamino-3-mercapto-N-mercaptomethylpropionamide,
(2R)-2-(acetylamino)-3-mercapto-N-(2-mercaptoethyl)propanamide,
2-acetylamino-3-mercapto-N-(3-mercaptopropyl)propionamide,
2-acetylamino-3-mercapto-N-(4-mercaptobutyl)propionamide,
2-(2-acetylamino-3-mercaptopropionylamino)-3-mercapto-3-methylbutyric acid,
2-acetylamino-3-mercapto-N-(1-mercaptomethylpropyl)propionamide,
2-acetylamino-N-(1-dimethylcarbamoyl-2-mercaptoethyl)-3-mercaptopropionamide,
N-acetyl-L-cysteinyl-L-cysteine,
N-(N-acetylcysteinyl)-L-cysteine,
N-(N-acetylcysteinyl)-DL-cysteine, ethyl N-acetyl-L-cysteinyl-D-cysteinate,
ethyl N-acetyl-L-cysteinyl-L-cysteinate,
2-acetamido-N-(1-carbamoyl-2-mercaptoethyl)-3-mercaptopropionamide,
ethyl N-acetyl-L-cysteinyl-L-cysteinyl-glycinate,
2-(2-acetylamino-3-mercaptopropionylamino)-4-mercaptobutyric acid,
2-(carboxymethylamino)-3-mercapto-N-mercaptomethylpropionamide,
2-(carboxymethylamino)-3-mercapto-N-(2-mercaptoethyl)propionamide,
2-(carboxymethylamino)-3-mercapto-N-(3-mercaptopropyl)propionamide,
2-(carboxymethylamino)-3-mercapto-N-(4-mercaptobutyl)propionamide,
2-(carboxymethylamino)-N-(1-carbamoyl-2-mercaptoethyl)-3-mercaptopropionamide,
2-[2-(carboxymethylamino)-3-mercaptopropionylamino]-3-mercaptopropionic acid,
[1-(1-carbamoyl-2-mercaptoethylcarbamoyl)-2-mercaptoethylamino]acetic acid,
2-(carboxymethylamino)-3-mercapto-N-(2-mercapto-1,1-dimethylethyl)propionamide,
N-[N-[N-(carboxymethyl)-L-cysteinyl]-L-cysteinyl]-D-valine,
2-amino-4-[2-mercapto-1-(mercaptomethylcarbamoyl)ethylcarbamoyl]butyric acid,
2-amino-4-[2-mercapto-1-(2-mercaptoethylcarbamoyl)ethylcarbamoyl]butyric acid,
2-amino-4-[2-mercapto-1-(3-mercaptopropylcarbamoyl)ethylcarbamoyl]butyric acid,
2-amino-4-[2-mercapto-1-(4-mercaptobutylcarbamoyl)ethylcarbamoyl]butyric acid,
L-γ-glutamyl-L-cysteinyl-L-cysteine,
2-[2-(4-amino-4-carboxybutyrylamino)-3-mercaptopropionylamino]-4-mercaptobutyric acid,
2-amino-4-[1-(1-carbamoyl-2-mercaptoethylcarbamoyl)-2-mercaptoethylcarbamoyl]butyric acid,
2-amino-4-[1-(1-dimethylcarbamoyl-2-mercaptoethylcarbamoyl)-2-mercaptoethylcarbamoyl]butyric acid,
2-amino-4-[2-mercapto-1-(2-mercapto-1,1-dimethylethylcarbamoyl)ethylcarbamoyl]butyric acid,
2-amino-4-[2-mercapto-1-(2-mercapto-1-ethylethylcarbamoyl)ethylcarbamoyl]butyric acid,
2-(2-aminoacetylamino)-3-mercapto-N-mercaptomethylpropionamide,
2-(2-aminoacetylamino)-3-mercapto-N-(2-mercaptoethyl)propionamide,
2-(2-aminoacetylamino)-3-mercapto-N-(3-mercaptopropyl)propionamide,
2-(2-aminoacetylamino)-3-mercapto-N-(4-mercaptobutyl)propionamide,
2-(2-aminoacetylamino)-3-mercapto-N-(5-mercaptopentyl)propionamide,
glycyl-L-cysteinyl-L-cysteine,
2-[2-(2-aminoacetylamino)-3-mercaptopropionylamino]-4-mercaptobutyric acid,
2-(2-aminoacetylamino)-3-mercapto-N-(2-mercapto-1,1-dimethylethyl)propionamide,
2-(2-aminoacetylamino)-3-mercapto-N-(1-mercaptomethylpropyl)propionamide,
4-carboxy-L-α-glutamyl-L-cysteinyl-L-cysteine,
(S)-N-[N-(5-amino-5-carboxy-1-oxopentyl)-L-homocysteinyl]-L-cysteine,
4-mercapto-N-mercaptomethylbutyramide,
4-mercapto-N-(2-mercaptoethyl)butyramide,
4-mercapto-N-(3-mercaptopropyl)butyramide,
N-(4-mercapto-1-oxobutyl)-L-cysteine,
4-mercapto-2-(3-mercaptopropionylamino)butyramide,
N-(1-dimethylcarbamoyl-2-mercaptoethyl)-4-mercaptobutyramide,
N-(4-mercapto-1-oxobutyl)-L-homocysteine,
4-mercapto-N-(2-mercapto-1,1-dimethylethyl)butyramide,
4-mercapto-N-(1-mercaptomethylpropyl)butyramide,
5-mercaptopentanoic acid mercaptomethylamide,
5-mercaptopentanoic acid (2-mercaptoethyl)amide,
N-(5-mercapto-1-oxopentyl)-L-cysteine,
5-mercapto-2-(3-mercaptopropionylamino)pentanamide,
N-(1-dimethylcarbamoyl-2-mercaptoethyl)-5-mercaptopentanamide,
5-mercapto-N-(2-mercapto-1,1-dimethylethyl)pentanamide,
5-mercapto-N-(1-mercaptomethylpropyl)pentanamide, and
6-mercaptohexanoic acid mercaptomethylamide, For example, the reducing agents of formula (I) may be chosen from:
2-mercapto-N-(mercaptomethyl)acetamide,
2-mercapto-N-(2-mercaptoethyl)acetamide,
2-mercapto-N-(3-mercaptopropyl)acetamide,
2-mercapto-N-(4-mercaptobutyl)acetamide,
2-mercapto-N-(5-mercaptopentyl)acetamide,
3-mercapto-2-(2-mercaptoacetylamino)propionamide,
3-mercapto-2-(2-mercaptoacetylamino)-N,N-dimethylpropionamide,
2-mercapto-N-(2-mercapto-1,1-dimethylethyl)acetamide,
2-mercapto-N-(1-mercaptomethylpropyl)acetamide,
N-(mercaptoacetyl)-L-cysteine,
N-(mercaptoacetyl)-L-homocysteine,
2-mercapto-N-mercaptomethylpropionamide,
2-mercapto-N-(2-mercaptoethyl)propionamide,
2-mercapto-N-(3-mercaptopropyl)propionamide,
2-mercapto-N-(4-mercaptobutyl)propionamide,
2-mercapto-N-(5-mercaptopentyl)propionamide,
mercapto-[(2-mercapto-1-oxopropyl)amino]acetic acid,
2-mercaptopropionyl-L-cysteine,
N-(1-carbamoyl-2-mercaptoethyl)-2-mercaptopropionamide,
N-(1-dimethylcarbamoyl-2-mercaptoethyl)-2-mercaptopropionamide,
4-mercapto-2-(2-mercaptopropionylamino)butyric acid,
2-mercapto-N-(2-mercapto-1,1-dimethylethyl)propionamide,
2-mercaptobutanoic acid mercaptomethylamide,
2-mercaptobutanoic acid (2-mercaptoethyl)amide,
2-mercaptobutanoic acid (3-mercaptopropyl)amide,
2-mercaptobutanoic acid (4-mercaptobutyl)amide,
2-mercaptopentanoic acid mercaptomethylamide,
2-mercaptopentanoic acid (2-mercaptoethyl)amide,
2-mercaptopentanoic acid (3-mercaptopropyl)amide,
3-mercapto-N-(2-mercaptoethyl)propanamide,
3-mercapto-N-mercaptomethylpropionamide,
3-mercapto-N-(3-mercaptopropyl)propionamide,
3-mercapto-N-(4-mercaptobutyl)propionamide,
N-(3-mercapto-1-oxopropyl)-L-cysteine,
3-mercapto-2-(3-mercaptopropionylamino)propionamide,
N-(1-dimethylcarbamoyl-2-mercaptoethyl)-3-mercaptopropionamide,
4-mercapto-2-(3-mercaptopropionylamino)butyric acid,
3-mercapto-N-(2-mercapto-1,1-dimethylethyl)propionamide,
3-mercapto-N-mercaptomethyl-2-methylpropionamide,
3-mercapto-N-(2-mercaptoethyl)-2-methylpropionamide,
3-mercapto-N-(3-mercaptopropyl)-2-methylpropionamide,
3-mercapto-N-(4-mercaptobutyl)-2-methylpropionamide, 3-mercapto-2-(3-mercapto-2-methylpropionylamino)propionic acid,
N-(1-carbamoyl-2-mercaptoethyl)-3-mercapto-2-methylpropionamide,
N-(1-dimethylcarbamoyl-2-mercaptoethyl)-3-mercapto-2-methylpropionamide,
3-mercapto-N-(2-mercapto-1,1-dimethylethyl)-2-methylpropionamide,
N-(3-mercapto-2-methyl-1-oxopropyl)-L-homocysteine,
N-mercaptomethyl-3-mercaptomethylsuccinamic acid,
N-(2-mercaptoethyl)-3-mercaptomethylsuccinamic acid,
N-(3-mercaptopropyl)-3-mercaptomethylsuccinamic acid,
N-(4-mercaptobutyl)-3-mercaptomethylsuccinamic acid,
N-(1-carboxy-2-mercaptoethyl)-3-mercaptomethylsuccinamic acid,
2-mercapto-N-mercaptomethyl-2-methylpropionamide,
2-mercapto-N-(2-mercaptoethyl)-2-methylpropanamide,
2-mercapto-N-(3-mercaptopropyl)-2-methylpropionamide,
2-mercapto-N-(4-mercaptobutyl)-2-methylpropionamide,
2-mercapto-N-(2-mercapto-1,1-dimethylethyl)-2-methylpropionamide,
2-mercapto-N-(2-mercapto-1-ethyl)-2-methylpropionamide,
N-(2-mercapto-2-methyl-1-oxopropyl)-L-cysteine,
N-(2-ethyl-2-mercapto-1-oxobutyl)-L-cysteine,
3-mercapto-N-mercaptomethyl-3-methylbutyramide,
3-mercapto-N-(2-mercaptoethyl)-3-methylbutanamide,
3-mercapto-N-(3-mercaptopropyl)-3-methylbutyramide,
N-(3-mercapto-3-methyl-1-oxobutyl)-L-cysteine,
N-(1-carbamoyl-2-mercaptoethyl)-3-mercapto-3-methylbutyramide,
N-(1-dimethylcarbamoyl-2-mercaptoethyl)-3-mercapto-3-methylbutyramide,
4-mercapto-2-(3-mercapto-3-methylbutyrylamino)butyric acid,
3-mercapto-N-mercaptomethyl-2,2-dimethylpropionamide,
3-mercapto-N-(2-mercaptoethyl)-2,2-dimethylpropionamide,
3-mercapto-N-(3-mercaptopropyl)-2,2-dimethylpropionamide,
3-mercapto-N-(4-mercaptobutyl)-2,2-dimethylpropionamide,
N-(3-mercapto-2,2-dimethyl-1-oxopropyl)-L-cysteine,
N-(1-carbamoyl-2-mercaptoethyl)-3-mercapto-2,2-dimethylpropionamide,
N-(1-dimethylcarbamoyl-2-mercaptoethyl)-3-mercapto-2,2-dimethylpropionamide,
N-[2-ethyl-2-(mercaptomethyl)-1-oxobutyl]-L-cysteine,
2-amino-3-mercapto-N-mercaptomethylpropionamide,
(2R)-2-amino-3-mercapto-N-(2-mercaptoethyl)propanamide,
(2S)-2-amino-3-mercapto-N-(2-mercaptoethyl)propanamide,
2-amino-3-mercapto-N-(3-mercaptopropyl)propionamide,
2-amino-3-mercapto-N-(4-mercaptobutyl)propionamide,
L-cysteinyl-L-cysteine,
2-amino-N-(1-carbamoyl-2-mercaptoethyl)-3-mercaptopropionamide,
2-amino-N-(1-carbamoyl-2-mercaptoethyl)-3-mercapto-N,N-dimethylpropionamide,
2-(2-amino-3-mercaptopropionylamino)-4-mercaptobutyric acid,
2-amino-3-mercapto-N-(2-mercapto-1,1-dimethylethyl)propionamide,
2-amino-3-mercapto-N-(2-mercapto-1-ethyl)propionamide,
2-acetylamino-3-mercapto-N-mercaptomethylpropionamide,
N-acetyl-L-cysteinyl-L-cysteine,
2-(carboxymethylamino)-3-mercapto-N-mercaptomethylpropionamide,
2-(carboxymethylamino)-3-mercapto-N-(2-mercaptoethyl)propionamide,
2-(carboxymethylamino)-3-mercapto-N-(3-mercaptopropyl)propionamide,
L-γ-glutamyl-L-cysteinyl-L-cysteine,
2-(2-aminoacetylamino)-3-mercapto-N-mercaptomethylpropionamide,
2-(2-aminoacetylamino)-3-mercapto-N-(2-mercaptoethyl)propionamide,
glycyl-L-cysteinyl-L-cysteine,
4-carboxy-L-α-glutamyl-L-cysteinyl-L-cysteine,
4-mercapto-N-mercaptomethylbutyramide,
4-mercapto-N-(2-mercaptoethyl)butyramide,
4-mercapto-N-(3-mercaptopropyl)butyramide,
N-(4-mercapto-1-oxobutyl)-L-cysteine,
4-mercapto-2-(3-mercaptopropionylamino)butyramide,
N-(1-dimethylcarbamoyl-2-mercaptoethyl)-4-mercaptobutyramide,
4-mercapto-N-(2-mercapto-1,1-dimethylethyl)butyramide,
4-mercapto-N-(1-mercaptomethylpropyl)butyramide,
5-mercaptopentanoic acid mercaptomethylamide,
5-mercaptopentanoic acid (2-mercaptoethyl)amide,
N-(5-mercapto-1-oxopentyl)-L-cysteine,
5-mercapto-2-(3-mercaptopropionylamino)pentanamide,
N-(1-dimethylcarbamoyl-2-mercaptoethyl)-5-mercaptopentanamide,
5-mercapto-N-(2-mercapto-1,1-dimethylethyl)pentanamide,
5-mercapto-N-(1-mercaptomethylpropyl)pentanamide, and
6-mercaptohexanoic acid mercaptomethylamide.

The process in accordance with the present disclosure for permanently reshaping keratin fibers comprises the application, to the keratin fibers, of a reducing composition comprising, as reducing agent, at least one compound of formula (I), and then an oxidizing (or fixing) composition, with or without an intermediate or subsequent step comprising rinsing or applying an intermediate composition. The hair is shaped using mechanical implements well known to those skilled in the art, such as curlers, the reducing composition being applied before or after the implements for reshaping the hair.

According to the present disclosure, the process for permanently reshaping keratin fibers can comprise, for example, reducing the disulphide bonds of keratin by application, for a period of time ranging from 5 minutes to 60 minutes, a reducing composition as defined above, and then, in reforming said bonds by application of an oxidizing composition or, optionally, by allowing the oxygen in the air to act.

For example, a reducing composition as defined above may be applied to wet hair rolled beforehand onto rollers that range from 2 mm to 30 mm in diameter, it being possible for the composition to be optionally applied as the hair is rolled; the reducing composition may then be allowed to act for a period of time ranging from 5 minutes to 60 minutes, such as from 10 minutes to 40 minutes, and then the hair is thoroughly rinsed, after which an oxidizing composition for reforming the disulphide bonds of keratin can be applied to the rolled hair for a period of application time ranging from 2 minutes to 10 minutes. After the rollers are removed, the hair is thoroughly rinsed.

After application of the reducing composition, the hair can also optionally be subjected to a thermal treatment by heating at a temperature ranging from 30° C. to 60° C. during all or part of the application time. In practice, this thermal treatment can be carried out for example, with a hairstyling hood, a hairdryer, an infrared ray-emitting device and other conventional heating devices.

The oxidation or oxidizing composition is of the type commonly used and can comprise, for example, as the at least one oxidizing agent, aqueous hydrogen peroxide, an alkaline bromate, a persalt, a polythionate or a mixture of alkaline bromate and of persalt. The aqueous hydrogen peroxide, when present, can be present in an amount ranging from 1 volume to 20 volumes, such as from 1 volume to 10 volumes; the alkaline bromate, when present, can be present in an amount ranging from 2% to 12% by weight; and the persalt, when present, can be present in an amount ranging from 0.1% to 15% by weight, relative to the total weight of the oxidizing composition. The pH of the oxidizing composition can range from 2 to 10. This oxidation can be carried out immediately or can be delayed, relative to the application of the composition comprising the at least one reducing agent as defined above.

The reshaping of keratin fibers according to the present disclosure can also comprise a process for relaxing or straightening keratin fibers, in which a reducing composition according to the present disclosure is applied to the keratin fibers, and then the keratin fibers are subjected to a mechanical reshaping enabling them to be fixed in their new shape, via an operation comprising smoothing out the keratin fibers with a large-toothed comb, with the back of a comb and/or with the hand. After a period of application time ranging from 5 minutes to 60 minutes, such as from 15 minutes to 45 minutes, a further smoothing out procedure is performed, followed by careful rinsing and application of an oxidizing or fixing composition as defined above, which is left to act for a period of time ranging from 2 minutes to 10 minutes, and then the keratin fibers are thoroughly rinsed.

In each of the processes described above, it is possible to also incorporate the use of a hot iron at a temperature ranging from 60° C. to 220° C., such as from 120° C. to 200° C.

Another aspect of the present disclosure is an aqueous reducing composition, which can be used in a process for permanently reshaping the hair, comprising, as reducing agent, at least one dimercaptoamide of formula (I) as described above.

In the permanent-waving compositions according to the present disclosure, the at least one reducing agent of formula (I) can be present in an amount ranging from 0.05% to 35%, such as from 1% to 20% by weight, relative to the total weight of the reducing composition.

The pH of the reducing composition as disclosed herein can range from 4 to 11, for instance, from 6 to 10, and can be obtained using an alkaline agent such as, by way of non-limiting example, aqueous ammonia, monoethanolamine, diethanolamine, triethanolamine, isopropylamine, 1,3-propanediamine, an alkali metal carbonate or bicarbonate or an ammonium carbonate or bicarbonate, an organic carbonate such as guanidine carbonate, or an alkali metal hydoxide, or using an acidifying agent such as, for example, hydrochloric acid, acetic acid, lactic acid, oxalic acid or boric acid, or alternatively using usual buffers, such as borate, phosphate, TRIS buffers, or the like.

The reducing composition can also comprise at least one other known reducing agent, such as, for example, thioglycolic acid or thiolactic acid and their ester and amide derivatives, for instance, glyceryl monothioglycolate, cysteamine and its $C_1$-$C_4$ acylated derivatives, such as N-acetylcysteamine or N-propionylcysteamine, cysteine, N-acetylcysteine, thiomalic acid, pantethein, 2,3-dimercaptosuccinic acid, alkali metal or alkaline-earth metal sulphites or bisulphites, the N-(mercaptoalkyl)-ω-hydroxyalkylamides described in European Patent Application No. EP 354 835 A, the N-mono- or N,N-dialkylmercapto-4-butyramides described in European Patent Application No. EP 368 763 A, the aminomercaptoalkylamides described in European Patent Application No. EP 432 000 A, the N-(mercaptoalkyl)succinamic acid and N-(mercaptoalkyl)succinimide derivatives described in European Patent Application No. EP 465 342 A, the alkylaminomercaptoalkylamides described in European Patent Application No. EP 514 282 A, the azeotropic mixture of 2-hydroxypropyl thioglycolate and of (2-hydroxy-1-methyl)ethyl thioglycolate described in French Patent Application No. FR 2 679 448 A, the mercaptoalkylaminoamides described in French Patent Application No. FR 2 692 481 A, the N-mercaptoalkylalkanediamides described in European Patent Application No. EP 653 202 A, and also the formamidinesulphinic acid derivatives described in International Application No. PCT/US01/43124.

The reducing composition may also comprise at least one surfactant chosen from nonionic, anionic, cationic and amphoteric type, and among these, non-limiting mention may be made of alkyl sulphates, alkylbenzene sulphates, alkyl ether sulphates, alkylsulphonates, quaternary ammonium salts, alkylbetaines, oxyethylenated alkylphenols, fatty acid alkanolamides, oxyethylenated fatty acid esters, and also other nonionic surfactants of the hydroxypropyl ether type.

When the reducing composition comprises at least one surfactant, said surfactant can be present in an amount of greater than or equal to 30% by weight, and may range, for example 0.5 and 10% by weight, relative to the total weight of the reducing composition.

With the aim of improving the cosmetic properties of the hair or else of attenuating or preventing the degradation thereof, the reducing composition may also comprise at least one treating agent chosen from cationic, anionic, non-ionic, and amphoteric treating agents.

Among the treating agents that may be used, non-limiting mention may be made of those described in French Patent Nos. 2,598,613 and 2,470,596. By way of non-limiting example, use may also be made, as treating agents, of linear or cyclic, volatile or nonvolatile, silicones and mixtures thereof, polydimethylsiloxanes, quaternized polyorganosiloxanes such as those described in French Patent No. 2 535 730, polyorganosiloxanes comprising aminoalkyl groups modified with alkoxycarbonylalkyl groups such as those described in U.S. Pat. No. 4,749,732, polyorganosiloxanes such as the polydimethylsiloxane-polyoxyalkyl copolymer of the Dimethicone Copolyol type, a polydimethylsiloxane comprising stearoxy end groups (stearoxy dimethicone), a polydimethylsiloxane-dialkylammonium acetate copolymer or a polydimethylsiloxane-polyalkylbetaine copolymer described in British Patent No. 2 197 352, polysiloxanes organomodified with mercapto or mercaptoalkyl groups such as those described in French Patent No. 1,530,369 and in European Patent Application No. EP 295 780, and also silanes such as stearoxytrimethylsilane.

The reducing composition may also further comprise at least one adjuvent such as cationic polymers, for instance those used in the compositions of French Patent Nos. 2 472 382 and 2 495 931, or alternatively cationic polymers of the ionene type, such as those used in the compositions of Luxembourg Patent No. 83703, basic amino acids (such as lysine or arginine) or acidic amino acids (such as glutamic acid or aspartic acid), peptides and derivatives thereof, protein hydrolysates, waxes, swelling agents, penetrating agents or agents for improving the efficacy of the reducing agent, such as the $SiO_2$/PDMS (polydimethylsiloxane) mixture, dimethylisosorbitol, urea and its derivatives, pyrrolidone, N-alkylpyrrolidones, thiamorpholinone, alkylene glycol alkyl ethers or dialkylene glycol alkyl ethers such as, for example propylene glycol monomethyl ether, dipropylene glycol monomethyl ether, ethylene glycol monoethyl ether and diethylene glycol monoethyl ether, $C_3$-$C_6$ alkanediols, such as, for example, 1,2-propanediol, 1,3-propanediol and 1,2-butanediol, 2-imidazolidinone, and also other compounds such as fatty alcohols, lanolin derivatives, active ingredients such as panthothenic acid, agents for preventing hair loss, antidandruff agents, thickeners, suspending agents, sequestering agents, opacifiers, colorants, sunscreens, and also fragrances and preserving agents, thickeners and gelling agents.

The reducing composition according to the present disclosure can be in aqueous form, such as in the form of a lotion that may or may not be thickened, of a cream or of a gel.

The reducing composition according to the present disclosure may be of the exothermic type, i.e. that may cause a certain amount of heating when it is applied to the hair, which may be pleasant for the individual undergoing the first step of the permanent-waving or of the hair-relaxing.

The reducing composition according to the present disclosure may also comprise at least one solvent, such as a $C_1$-$C_6$ monoalcohol, for instance ethanol, propanol, isopropanol or butanol, and/or a polyol such as glycerol, which may be present in an amount ranging from 0.01% to 20% by weight, such as from 0.1% to 15% by weight, relative to the total weight of the composition.

The carrier of the compositions according to the present disclosure can, for example, consist of water, or comprise an aqueous-alcoholic solution comprising water and at least one solvent as defined above.

When the reducing composition as disclosed herein is intended for a hair-relaxing or hair-straightening process, the reducing composition can be, for example, in the form of a thickened cream so as to keep the hair as stiff as possible. These creams are prepared in the form of "heavy" emulsions, for example based on glyceryl stearate, glycyl stearate, self-emulsifiable waxes or fatty alcohols.

It is also possible to use liquids or gels comprising thickeners such as carboxyvinyl polymers or copolymers that "stick" the hairs together and keep them in a smooth position during the application time.

The present disclosure also relates to a kit, for instance for permanently reshaping the hair, comprising, in at least one first compartment, a reducing composition in accordance with the present disclosure comprising at least one compound of formula (I) and, in at least one second compartment, an oxidizing composition.

Another aspect of the present disclosure is also, as novel compounds, the dimercaptoamides of formula (II), and the organic and inorganic salts thereof:

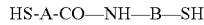

HS-A-CO—NH—B—SH　　　　(II)

wherein:

(i) A is a radical $CH_2$, and B is chosen from $(CH_2)_x$ radicals, wherein x is an integer chosen from 2, 3, 4 or 5; $C(CH_3)_2$—$CH_2$ radicals; CH(Et)—$CH_2$ radicals; CH(CO—NR1R2)-$CH_2$ radicals; and CH(CO—NR1R2)-$CH_2$—$CH_2$ radicals in which R1 and R2, which may be identical or different, are chosen from hydrogen atoms, and methyl, ethyl and 2-hydroxypropyl radicals;

(ii) A is a radical CH($CH_3$) and B is chosen from $(CH_2)_x$ radicals wherein x is an integer chosen from 1, 2, 3, 4 or 5; $C(CH_3)_2$—$CH_2$ radicals; CH(Et)-$CH_2$ radicals; CH(COOH)—$CH_2$—$CH_2$ radicals; CH(CO—NR1R2)-$CH_2$ and CH(CO—NR1R2)-$CH_2$—$CH_2$ radicals in which R1 and R2, which may be identical or different, are chosen from hydrogen atoms, and methyl, ethyl and 2-hydroxypropyl radicals;

(iii) A is chosen from CH—R3 radicals wherein R3 is chosen from linear and branched $C_2$-$C_5$ alkyl radicals, and B is chosen from $(CH_2)_x$ radicals wherein x is an integer chosen from 1, 2, 3, 4 or 5; $C(CH_3)_2$—$CH_2$ radicals; CH(Et)-$CH_2$ radicals; CH(COOH)—$CH_2$ radicals; CH(COOH)—$CH_2$—$CH_2$ radicals; CH(CO—NR1R2)-$CH_2$ radicals; and CH(CO—NR1R2)-$CH_2$—$CH_2$ radicals wherein R1 and R2, which may be identical or different, ar chosen from hydogen atoms and methyl, ethyl and 2-hydroxypropyl radicals;

(iv) A is chosen from $CH_2$—$CH_2$ and $C(CH_3)_2$—$CH_2$ radicals, and B is chosen from $(CH_2)_x$ radicals wherein x is an integer chosen from 1, 3 or 4; $C(CH_3)_2$—$CH_2$ radicals; CH(Et)-$CH_2$ radicals; CH(COOH)—$CH_2$—$CH_2$ radicals; CH(CO—NR1R2)-$CH_2$ radicals and CH(CO—NR1R2)-$CH_2$—$CH_2$ radicals wherein R1 and R2, which may be identical or different, are chosen from hydrogen atoms and methyl, ethyl and 2-hydroxypropyl radicals, (v) A is a radical $CH_2$—CH($CH_3$), and B is chosen from $(CH_2)_x$ radicals wherein x is an integer chosen from 1, 2, 3 or 4; $C(CH_3)_2$—$CH_2$ radicals; CH(Et)-$CH_2$ radicals; CH(COOH)—$CH_2$ radicals; CH(CO—NR1R2)-$CH_2$ radicals; and CH(CO—NR1R2)-$CH_2$—$CH_2$ radicals, wherein R1 and R2, which may be identical or different, are chosen from hydrogen atoms and methyl, ethyl and 2-hydroxypropyl radicals;

(vi) A is chosen from $CH_2$—CH—R4 radicals wherein R4 is chosen from phenyl radicals, COO—$CH_3$ radicals, and COO—$CH_2$—$CH_3$ radicals, and B is chosen from $(CH_2)_x$ radicals wherein x is an integer chosen from 1, 2, 3 or 4; $C(CH_3)_2$—$CH_2$ radicals; CH(Et)-$CH_2$ radicals; CH(COOH)—$CH_2$—$CH_2$ radicals; CH(CO—NR1R2)-$CH_2$ radicals; and CH(CO—NR1R2)-$CH_2$—$CH_2$ radicals, wherein R1 and R2, which may be identical or different, are chosen from hydrogen atoms and methyl, ethyl and 2-hydroxypropyl radicals;

(vii) A is chosen from $CH_2$—CH($CH_2$—COOH) and $CH_2$—CH(NH—$CH_2$—COOH) radicals, and B is chosen from $(CH_2)_x$ radicals wherein x is an integer chosen from 1, 2, 3 or 4; $C(CH_3)_2$—$CH_2$ radicals; CH(Et)-$CH_2$ radicals; CH(COOH)—$CH_2$ radicals; CH(COOH)—$CH_2$—$CH_2$ radicals; CH(CO—NR1R2)-$CH_2$ radicals; and CH(CO—NR1R2)-$CH_2$—$CH_2$ radicals, wherein R1 and R2, which may be identical or different, are chosen from hydrogen atoms and methyl, ethyl and 2-hydroxypropyl radicals;

(viii) A is a radical $C(CH_3)_2$, and B is chosen from $(CH_2)_x$ radicals, wherein x is an integer chosen from 1, 3, 4 or 5; $C(CH_3)_2$—$CH_2$ radicals; CH(Et)-$CH_2$ radicals; CH(CO—NH$CH_3$)—$CH_2$ radicals; CH(CO—NHEt)-$CH_2$ radicals; CH(CO—NH—$CH_2$—CHOH—$CH_3$)—$CH_2$ radicals; and CH(CO—NR1R2)-$CH_2$—$CH_2$ radicals, wherein R1 and R2, which may be identical or different, are chosen from hydrogen atoms and methyl, ethyl and 2-hydroxypropyl radicals;

(ix) A is a radical $C(Et)_2$, and B is chosen from $(CH_2)_x$ radicals wherein x is an integer ranging from 1, 2, 3, 4 or 5; $C(CH_3)_2$—$CH_2$ radicals; CH(Et)-$CH_2$ radicals; CH(COOH)—$CH_2$—$CH_2$ radicals; CH(CO—NR1R2)-$CH_2$ radicals, and CH(CO—NR1R2)-$CH_2$—$CH_2$ radicals, wherein R1 and R2, which may be identical or different, are chosen from hydrogen atoms and methyl, ethyl and 2-hydroxypropyl radicals;

(x) A is chosen from $CH_2$—$C(CH_3)_2$ and CH($CH_2$-Ph) radicals, and B is chosen from $(CH_2)_x$ radicals wherein x is an integer chosen from 1, 2, 3 or 4; $C(CH_3)_2$—$CH_2$ radicals; CH(Et)-$CH_2$ radicals; CH(CO—NR1R2)-$CH_2$ radicals; and CH(CO—NR1R2)-CH₂—CH₂ radicals, wherein R1 and R2, which may be identical or different, are chosen from hydrogen atoms, and methyl, ethyl and 2-hydroxypropyl radicals;

(xi) A is a radical CH₂—C(Et)₂, and B is chosen from (CH₂)$_x$ radicals wherein x is an integer chosen from 1, 2, 3 or 4; C(CH₃)₂—CH₂ radicals; CH(Et)-CH₂ radicals; CH(COOH)—CH₂—CH₂ radicals; CH(CO—NR1R2)-CH₂ radicals; and CH(CO—NR1R2)-CH₂—CH₂ radicals, wherein R1 and R2, which may be identical or different, are chosen from hydrogen atoms, and methyl, ethyl and 2-hydroxypropyl radicals;

(xii) A is a radical CH₂—CH(NH₂), and B is chosen from (CH₂)$_x$ radicals wherein x is an integer chosen from 1, 3 or 4; C(CH₃)₂—CH₂ radicals; CH(Et)-CH₂ radicals; CH(COOH)—CH₂—CH₂ radicals; CH(CO—NR1R2)-CH₂ radicals; and CH(CO—NR1R2)-CH₂—CH₂ radicals, wherein R1 and R2, which may be identical or different, are chosen from hydrogen atoms, and methyl, ethyl and 2-hydroxypropyl radicals, (xiii) A is a radical CH₂—CH(NHAc), and B is chosen from (CH₂)$_x$ radicals wherein x is an integer chosen from 1, 3 or 4; C(CH₃)₂—CH₂ radicals; CH(Et)-CH₂ radicals; CH(COOH)—CH₂—CH₂ radicals; CH(CO—NH—CH₃)—CH₂ radicals; CH(CO—NH-Et)-CH₂ radicals; CH(CO—N(CH₃)₂)—CH₂ radicals; and CH(CO—NR1R2)-CH₂—CH₂ radicals wherein R1 and R2, which may be identical or different, are chosen from hydrogen atoms, and methyl, ethyl and 2-hydroxypropyl radicals;

(xiv) A is chosen from CH₂—CH(NH—CO—CH₂—CH₂—CH(NH₂)COOH), CH₂—CH(NH—CO—CH₂—NH₂), CH₂—CH(NH—CO—CH(NH₂)—CH₂—CH(COOH)₂, and CH₂—CH(NH—CO—CH₂—CH₂—CH₂—CH(NH₂)COOH) radicals, and B is chosen from (CH₂)$_x$ radicals wherein x is an integer chosen from 1, 2, 3 or 4; C(CH₃)₂—CH₂ radicals; CH(Et)-CH₂ radicals; CH(COOH)—CH₂—CH₂ radicals; CH(CO—NR1R2)-CH₂ radicals; and CH(CO—NR1R2)-CH₂—CH₂ radicals, wherein R1 and R2, which may be identical or different, are chosen from hydrogen atoms, and methyl, ethyl and 2-hydroxypropyl radicals;

(xv) A is a radical (CH₂)₃, and B is chosen from (CH₂)$_x$ radicals wherein x is an integer chosen from 1, 2 or 3; C(CH₃)₂—CH₂ radicals; CH(Et)-CH₂ radicals; CH(COOH)—CH₂ radicals; CH(COOH)—CH₂—CH₂ radicals; CH(CO—NR1R2)-CH₂ radicals, and CH(CO—NR1R2)-CH₂—CH₂ radicals, wherein R1 and R2, which may be identical or different, are chosen from hydrogen atoms, and methyl, ethyl and 2-hydroxypropyl radicals;

(xvi) A is a radical (CH₂)₄, and B is chosen from (CH₂)$_x$ radicals wherein x is an integer chosen from 1 or 2; C(CH₃)₂—CH₂ radicals; CH(Et)-CH₂ radicals; CH(COOH)—CH₂ radicals; CH(COOH)—CH₂—CH₂ radicals; CH(CO—NR1R2)-CH₂ radicals; and CH(CO—NR1R2)-CH₂—CH₂ radicals, wherein R1 and R2, which may be identical or different, are chosen from hydrogen atoms, and methyl, ethyl, and 2-hydroxypropyl radicals;

(xvii) A is a radical (CH₂)₅, and B is a radical CH₂; or (xviii) A is a radical CH-Ph, and B is chosen from (CH₂)$_x$ radicals wherein x is an integer chosen from 1, 2, 3, 4 or 5; C(CH₃)₂—CH₂ radicals; CH(Et)-CH₂ radicals; CH(COOH)—CH₂ radicals; CH(COOH)—CH₂—CH₂ radicals; CH(CO—NR1R2)-CH₂ radicals; and CH(CO—NR1R2)-CH₂—CH₂ radicals, wherein R1 and R2, which may be identical or different, are chosen from hydrogen atoms, and methyl, ethyl, and 2-hydroxypropyl radicals.

The compounds of formula (II) can be used in the same manner as the compounds of formula (I) mentioned above.

Among the compounds of formula (II) that may be used as disclosed herein, non-limiting mention may be made of, for example:

2-mercapto-N-(2-mercaptoethyl)acetamide,
2-mercapto-N-(3-mercaptopropyl)acetamide,
2-mercapto-N-(4-mercaptobutyl)acetamide,
2-mercapto-N-(5-mercaptopentyl)acetamide,
3-mercapto-2-(2-mercaptoacetylamino)propionamide,
3-mercapto-2-(2-mercaptoacetylamino)-N,N-dimethylpropionamide,
2-mercapto-N-(2-mercapto-1,1-dimethylethyl)acetamide,
2-mercapto-N-(1-mercaptomethylpropyl)acetamide,
2-mercapto-N-mercaptomethylpropionamide,
2-mercapto-N-(2-mercaptoethyl)propionamide,
2-mercapto-N-(3-mercaptopropyl)propionamide,
2-mercapto-N-(4-mercaptobutyl)propionamide,
2-mercapto-N-(5-mercaptopentyl)propionamide,
N-(1-carbamoyl-2-mercaptoethyl)-2-mercaptopropionamide,
N-(1-dimethylcarbamoyl-2-mercaptoethyl)-2-mercaptopropionamide,
4-mercapto-2-(2-mercaptopropionylamino)butyric acid,
2-mercapto-N-(2-mercapto-1,1-dimethylethyl)propionamide,
2-mercaptobutanoic acid mercaptomethylamide,
2-mercaptobutanoic acid (2-mercaptoethyl)amide,
2-mercaptobutanoic acid (3-mercaptopropyl)amide,
2-mercaptobutanoic acid (4-mercaptobutyl)amide,
2-mercaptobutanoic acid (5-mercaptopentyl)amide,
2-mercaptobutanoic acid (1-carbamoyl-2-mercaptoethyl)amide,
N-(1-dimethylcarbamoyl-2-mercaptoethyl)-2-mercaptobutyramide,
2-mercaptobutanoic acid (1-carbamoyl-3-mercaptopropyl)amide,
2-mercaptobutanoic acid (2-mercapto-1,1-dimethylethyl)amide,
2-mercaptopentanoic acid mercaptomethylamide,
2-mercaptopentanoic acid (2-mercaptoethyl)amide,
2-mercaptopentanoic acid (3-mercaptopropyl)amide,
2-mercaptopentanoic acid (4-mercaptobutyl)amide,
2-mercaptopentanoic acid (5-mercaptopentyl)amide,
3-mercapto-2-(2-mercaptopentanoylamino)propionic acid,
2-mercaptopentanoic acid (1-carbamoyl-2-mercaptoethyl)amide,
2-mercaptopentanoic acid (1-dimethylcarbamoyl-2-mercaptoethyl)amide,
2-mercaptopentanoic acid (1-carbamoyl-3-mercaptopropyl)amide,
2-mercaptopentanoic acid (2-mercapto-1,1-dimethylethyl)amide,
3-mercapto-N-mercaptomethylpropionamide,
3-mercapto-N-(3-mercaptopropyl)propionamide,
3-mercapto-N-(4-mercaptobutyl)propionamide,
3-mercapto-2-(3-mercaptopropionylamino)propionamide,
N-(1-dimethylcarbamoyl-2-mercaptoethyl)-3-mercaptopropionamide,
4-mercapto-2-(3-mercaptopropionylamino)butyric acid,
3-mercapto-N-(2-mercapto-1,1-dimethylethyl)propionamide,
3-mercapto-N-mercaptomethyl-2-methylpropionamide,
3-mercapto-N-(2-mercaptoethyl)-2-methylpropionamide,
3-mercapto-N-(3-mercaptopropyl)-2-methylpropionamide,
3-mercapto-N-(4-mercaptobutyl)-2-methylpropionamide,
3-mercapto-2-(3-mercapto-2-methylpropionylamino)propionic acid, N-(1-carbamoyl-2-mercaptoethyl)-3-mercapto-2-methylpropionamide,
N-(1-dimethylcarbamoyl-2-mercaptoethyl)-3-mercapto-2-methylpropionamide,
3-mercapto-N-(2-mercapto-1,1-dimethylethyl)-2-methylpropionamide,
N-mercaptomethyl-3-mercaptomethylsuccinamic acid,
N-(2-mercaptoethyl)-3-mercaptomethylsuccinamic acid,
N-(3-mercaptopropyl)-3-mercaptomethylsuccinamic acid,
N-(4-mercaptobutyl)-3-mercaptomethylsuccinamic acid,
N-(1-carboxy-2-mercaptoethyl)-3-mercaptomethylsuccinamic acid,
N-(1-carboxy-3-mercaptopropyl)-3-mercaptomethylsuccinamic acid,
N-(2-mercapto-1,1-dimethylethyl)-3-mercaptomethylsuccinamic acid,
N-(2-mercapto-1-ethyl)-3-mercaptomethylsuccinamic acid,
2-mercapto-N-mercaptomethyl-2-methylpropionamide,
2-mercapto-N-(3-mercaptopropyl)-2-methylpropionamide,
2-mercapto-N-(4-mercaptobutyl)-2-methylpropionamide,
2-mercapto-N-(5-mercaptopentyl)-2-methylpropionamide,
2-mercapto-N-(2-mercapto-1,1-dimethylethyl)-2-methylpropionamide,
2-mercapto-N-(2-mercapto-1-ethyl)-2-methylpropionamide,
3-mercapto-N-mercaptomethyl-3-methylbutyramide,
3-mercapto-N-(3-mercaptopropyl)-3-methylbutyramide,
3-mercapto-N-(4-mercaptobutyl)-3-methylbutyramide,
N-(1-carbamoyl-2-mercaptoethyl)-3-mercapto-3-methylbutyramide,
N-(1-dimethylcarbamoyl-2-mercaptoethyl)-3-mercapto-3-methylbutyramide,
4-mercapto-2-(3-mercapto-3-methylbutyrylamino)butyric acid,
3-mercapto-N-(2-mercapto-1,1-dimethylethyl)-3-methylbutyramide,
3-mercapto-N-(2-mercapto-1-ethyl)-3-methylbutyramide,
3-mercapto-N-mercaptomethyl-2,2-dimethylpropionamide,
3-mercapto-N-(2-mercaptoethyl)-2,2-dimethylpropionamide,
3-mercapto-N-(3-mercaptopropyl)-2,2-dimethylpropionamide,
3-mercapto-N-(4-mercaptobutyl)-2,2-dimethylpropionamide,
3-mercapto-N-(2-mercapto-1,1-dimethylethyl)-2,2-dimethylpropionamide,
N-(1-carbamoyl-2-mercaptoethyl)-3-mercapto-2,2-dimethylpropionamide,
N-(1-dimethylcarbamoyl-2-mercaptoethyl)-3-mercapto-2,2-dimethylpropionamide,
2-amino-3-mercapto-N-mercaptomethylpropionamide,
2-amino-3-mercapto-N-(3-mercaptopropyl)propionamide,
2-amino-3-mercapto-N-(4-mercaptobutyl)propionamide,
2-amino-N-(1-carbamoyl-2-mercaptoethyl)-3-mercaptopropionamide,
2-amino-N-(1-carbamoyl-2-mercaptoethyl)-3-mercapto-N,N-dimethylpropionamide,
2-(2-amino-3-mercaptopropionylamino)-4-mercaptobutyric acid,
2-amino-3-mercapto-N-(2-mercapto-1,1-dimethylethyl)propionamide,
2-amino-3-mercapto-N-(2-mercapto-1-ethyl)propionamide,
2-acetylamino-3-mercapto-N-mercaptomethylpropionamide,
2-acetylamino-3-mercapto-N-(3-mercaptopropyl)propionamide,
2-acetylamino-3-mercapto-N-(4-mercaptobutyl)propionamide,
2-(2-acetylamino-3-mercaptopropionylamino)-3-mercapto-3-methylbutyric acid,
2-acetylamino-3-mercapto-N-(1-mercaptomethylpropyl)propionamide,
2-acetylamino-N-(1-dimethylcarbamoyl-2-mercaptoethyl)-3-mercaptopropionamide,
2-(2-acetylamino-3-mercaptopropionylamino)-4-mercaptobutyric acid,
2-(carboxymethylamino)-3-mercapto-N-mercaptomethylpropionamide,
2-(carboxymethylamino)-3-mercapto-N-(2-mercaptoethyl)propionamide,
2-(carboxymethylamino)-3-mercapto-N-(3-mercaptopropyl)propionamide,
2-(carboxymethylamino)-3-mercapto-N-(4-mercaptobutyl)propionamide,
2-(carboxymethylamino)-N-(1-carbamoyl-2-mercaptoethyl)-3-mercaptopropionamide,
2-[2-(carboxymethylamino)-3-mercaptopropionylamino]-3-mercaptopropionic acid,
[1-(1-carbamoyl-2-mercaptoethylcarbamoyl)-2-mercaptoethylamino]acetic acid,
2-(carboxymethylamino)-3-mercapto-N-(2-mercapto-1,1-dimethylethyl)propionamide,
2-amino-4-[2-mercapto-1-(mercaptomethylcarbamoyl)ethylcarbamoyl]butyric acid,
2-amino-4-[2-mercapto-1-(2-mercaptoethylcarbamoyl)ethylcarbamoyl]butyric acid,
2-amino-4-[2-mercapto-1-(3-mercaptopropylcarbamoyl)ethylcarbamoyl]butyric acid,
2-amino-4-[2-mercapto-1-(4-mercaptobutylcarbamoyl)ethylcarbamoyl]butyric acid,
2-[2-(4-amino-4-carboxybutyrylamino)-3-mercaptopropionylamino]4-mercaptobutyric acid,
2-amino-4-[1-(1-carbamoyl-2-mercaptoethylcarbamoyl)-2-mercaptoethylcarbamoyl]butyric acid,
2-amino-4-[1-(1-dimethylcarbamoyl-2-mercaptoethylcarbamoyl)-2-mercaptoethylcarbamoyl]butyric acid,
2-amino-4-[2-mercapto-1-(2-mercapto-1,1-dimethylethylcarbamoyl)ethylcarbamoyl]butyric acid,
2-amino-4-[2-mercapto-1-(2-mercapto-1-ethylethylcarbamoyl)ethylcarbamoyl]butyric acid,
2-(2-aminoacetylamino)-3-mercapto-N-mercaptomethylpropionamide,
2-(2-aminoacetylamino)-3-mercapto-N-(2-mercaptoethyl)propionamide,
2-(2-aminoacetylamino)-3-mercapto-N-(3-mercaptopropyl)propionamide,
2-(2-aminoacetylamino)-3-mercapto-N-(4-mercaptobutyl)propionamide,
2-(2-aminoacetylamino)-3-mercapto-N-(5-mercaptopentyl)propionamide,
2-[2-(2-aminoacetylamino)-3-mercaptopropionylamino]4-mercaptobutyric acid,
2-(2-aminoacetylamino)-3-mercapto-N-(2-mercapto-1,1-dimethylethyl)propionamide,
2-(2-aminoacetylamino)-3-mercapto-N-(1-mercaptomethylpropyl)propionamide,
4-mercapto-N-mercaptomethylbutyramide,
4-mercapto-N-(2-mercaptoethyl)butyramide,
4-mercapto-N-(3-mercaptopropyl)butyramide,
N-(4-mercapto-1-oxobutyl)-L-cysteine,
4-mercapto-2-(3-mercaptopropionylamino)butyramide,
N-(1-dimethylcarbamoyl-2-mercaptoethyl)-4-mercaptobutyramide, N-(4-mercapto-1-oxobutyl)-L-homocysteine,
4-mercapto-N-(2-mercapto-1,1-dimethylethyl)butyramide,
4-mercapto-N-(1-mercaptomethylpropyl)butyramide,
5-mercaptopentanoic acid mercaptomethylamide,
5-mercaptopentanoic acid (2-mercaptoethyl)amide,
N-(5-mercapto-1-oxopentyl)-L-cysteine,
5-mercapto-2-(3-mercaptopropionylamino)pentanamide,
N-(1-dimethylcarbamoyl-2-mercaptoethyl)-5-mercaptopentanamide,
5-mercapto-N-(2-mercapto-1,1-dimethylethyl)pentanamide,
5-mercapto-N-(1-mercaptomethylpropyl)pentanamide, and
6-mercaptohexanoic acid mercaptomethylamide, For example, the compounds of formula (II) may be chosen from:
2-mercapto-N-(2-mercaptoethyl)acetamide,
2-mercapto-N-(3-mercaptopropyl)acetamide,
2-mercapto-N-(4-mercaptobutyl)acetamide,
2-mercapto-N-(5-mercaptopentyl)acetamide,
3-mercapto-2-(2-mercaptoacetylamino)propionamide,
3-mercapto-2-(2-mercaptoacetylamino)-N,N-dimethylpropionamide,
2-mercapto-N-(2-mercapto-1,1-dimethylethyl)acetamide,
2-mercapto-N-(1-mercaptomethylpropyl)acetamide,
2-mercapto-N-mercaptomethylpropionamide,
2-mercapto-N-(2-mercaptoethyl)propionamide,
2-mercapto-N-(3-mercaptopropyl)propionamide,
2-mercapto-N-(4-mercaptobutyl)propionamide,
2-mercapto-N-(5-mercaptopentyl)propionamide,
N-(1-carbamoyl-2-mercaptoethyl)-2-mercaptopropionamide,
N-(1-dimethylcarbamoyl-2-mercaptoethyl)-2-mercaptopropionamide,
4-mercapto-2-(2-mercaptopropionylamino)butyric acid,
2-mercapto-N-(2-mercapto-1,1-dimethylethyl)propionamide,
2-mercaptobutanoic acid mercaptomethylamide,
2-mercaptobutanoic acid (2-mercaptoethyl)amide,
2-mercaptobutanoic acid (3-mercaptopropyl)amide,
2-mercaptobutanoic acid (4-mercaptobutyl)amide,
2-mercaptopentanoic acid mercaptomethylamide,
2-mercaptopentanoic acid (2-mercaptoethyl)amide,
2-mercaptopentanoic acid (3-mercaptopropyl)amide,
3-mercapto-N-mercaptomethylpropionamide,
3-mercapto-N-(3-mercaptopropyl)propionamide,
3-mercapto-2-(3-mercaptopropionylamino)propionamide,
N-(1-dimethylcarbamoyl-2-mercaptoethyl)-3-mercaptopropionamide,
4-mercapto-2-(3-mercaptopropionylamino)butyric acid,
3-mercapto-N-(2-mercapto-1,1-dimethylethyl)propionamide,
3-mercapto-N-mercaptomethyl-2-methylpropionamide,
3-mercapto-N-(2-mercaptoethyl)-2-methylpropionamide,
3-mercapto-N-(3-mercaptopropyl)-2-methylpropionamide,
3-mercapto-N-(4-mercaptobutyl)-2-methylpropionamide,
3-mercapto-2-(3-mercapto-2-methylpropionylamino)propionic acid,
N-(1-carbamoyl-2-mercaptoethyl)-3-mercapto-2-methylpropionamide,
N-(1-dimethylcarbamoyl-2-mercaptoethyl)-3-mercapto-2-methylpropionamide,
3-mercapto-N-(2-mercapto-1,1-dimethylethyl)-2-methylpropionamide,
N-mercaptomethyl-3-mercaptomethylsuccinamic acid,
N-(2-mercaptoethyl)-3-mercaptomethylsuccinamic acid,
N-(3-mercaptopropyl)-3-mercaptomethylsuccinamic acid,
N-(4-mercaptobutyl)-3-mercaptomethylsuccinamic acid,
N-(1-carboxy-2-mercaptoethyl)-3-mercaptomethylsuccinamic acid,
2-mercapto-N-mercaptomethyl-2-methylpropionamide,
2-mercapto-N-(3-mercaptopropyl)-2-methylpropionamide,
2-mercapto-N-(4-mercaptobutyl)-2-methylpropionamide,
2-mercapto-N-(2-mercapto-1,1-dimethylethyl)-2-methylpropionamide,
2-mercapto-N-(2-mercapto-1-ethyl)-2-methylpropionamide,
3-mercapto-N-mercaptomethyl-3-methylbutyramide,
3-mercapto-N-(3-mercaptopropyl)-3-methylbutyramide,
N-(1-carbamoyl-2-mercaptoethyl)-3-mercapto-3-methylbutyramide,
N-(1-dimethylcarbamoyl-2-mercaptoethyl)-3-mercapto-3-methylbutyramide,
4-mercapto-2-(3-mercapto-3-methylbutyrylamino)butyric acid,
3-mercapto-N-mercaptomethyl-2,2-dimethylpropionamide,
3-mercapto-N-(2-mercaptoethyl)-2,2-dimethylpropionamide,
3-mercapto-N-(3-mercaptopropyl)-2,2-dimethylpropionamide,
3-mercapto-N-(4-mercaptobutyl)-2,2-dimethylpropionamide,
N-(1-carbamoyl-2-mercaptoethyl)-3-mercapto-2,2-dimethylpropionamide,
N-(1-dimethylcarbamoyl-2-mercaptoethyl)-3-mercapto-2,2-dimethylpropionamide,
2-amino-3-mercapto-N-mercaptomethylpropionamide,
2-amino-3-mercapto-N-(3-mercaptopropyl)propionamide,
2-amino-3-mercapto-N-(4-mercaptobutyl)propionamide,
2-amino-N-(1-carbamoyl-2-mercaptoethyl)-3-mercaptopropionamide,
2-amino-N-(1-carbamoyl-2-mercaptoethyl)-3-mercapto-N N-dimethylpropionamide,
2-(2-amino-3-mercaptopropionylamino)-4-mercaptobutyric acid,
2-amino-3-mercapto-N-(2-mercapto-1,1-dimethylethyl)propionamide,
2-amino-3-mercapto-N-(2-mercapto-1-ethyl)propionamide,
2-acetylamino-3-mercapto-N-mercaptomethylpropionamide,
2-(carboxymethylamino)-3-mercapto-N-mercaptomethylpropionamide,
2-(carboxymethylamino)-3-mercapto-N-(2-mercaptoethyl)propionamide,
2-(carboxymethylamino)-3-mercapto-N-(3-mercaptopropyl)propionamide
2-(2-aminoacetylamino)-3-mercapto-N-mercaptomethylpropionamide,
2-(2-aminoacetylamino)-3-mercapto-N-(2-mercaptoethyl)propionamide,
4-mercapto-N-mercaptomethylbutyramide,
4-mercapto-N-(2-mercaptoethyl)butyramide,
4-mercapto-N-(3-mercaptopropyl)butyramide,
N-(4-mercapto-1-oxobutyl)-L-cysteine,
4-mercapto-2-(3-mercaptopropionylamino)butyramide,
N-(1-dimethylcarbamoyl-2-mercaptoethyl)-4-mercaptobutyramide,
4-mercapto-N-(2-mercapto-1,1-dimethylethyl)butyramide,
4-mercapto-N-(1-mercaptomethylpropyl)butyramide,
5-mercaptopentanoic acid mercaptomethylamide,
5-mercaptopentanoic acid (2-mercaptoethyl)amide,
N-(5-mercapto-1-oxopentyl)-L-cysteine,
5-mercapto-2-(3-mercaptopropionylamino)pentanamide,
N-(1-dimethylcarbamoyl-2-mercaptoethyl)-5-mercaptopentanamide, 5-mercapto-N-(2-mercapto-1,1-dimethylethyl)pentanamide,
5-mercapto-N-(1-mercaptomethylpropyl)pentanamide, and
6-mercaptohexanoic acid mercaptomethylamide.

The present disclosure also relates to processes for preparing the novel dimercaptoamides of formula (II).

The dimercaptoamides of formula (II) can be prepared according to a process comprising the reaction of a protected mercapto acid halide of formula P—S-A-CO—X, with a protected aminothiol of formula $H_2N$—B—S—P, with P being a thiol function-protecting group such as, for example, a trityl, acetyl or benzyl group, and X being chlorine or bromine, in an aprotic solvent, in the presence of an agent intended to capture the released hydrochloric or hydrobromic acid, such as, for example, a tertiary amine, so as to form a protected dimercaptoamide of formula P—S-A-CO—NH—B—S—P; and the deprotection of the protected dimercaptoamide by hydrolysis or by reduction.

They may also be prepared by a process comprising the reaction of a mercapto acid of formula HS-A-COOH with an aminothiol of formula $H_2N$—B—SH, in the presence of a coupling and/or dehydrating agent, in an aprotic solvent.

They may also be prepared by a process comprising the reaction of a mercapto ester of formula HS-A-COOR, with R being a methyl or ethyl radical, and with an aminothiol of formula $H_2N$—B—SH, at a temperature ranging from 30° C. to 180° C.

They may also be prepared by a process comprising the reaction of a halogenated acid halide of formula X-A-COCl with a haloamine of formula $H_2N$—B—X, wherein X is chosen from chlorine and bromine atoms, in an aprotic solvent and in the presence of an agent intended to capture the released hydrochloric or hydrobromic acid, so as to form a dihaloamide of formula X-A-CO—NH—B—X, and then the conversion of the dihaloamide obtained into a dimercaptoamide of formula (II), either by direct reaction with hydrogen sulphide in an appropriate solvent, or by reaction with thioacetic acid, for instance in salified form, followed by acid or alkaline hydrolysis of the di(S-acetyl)mercaptoamide, or alternatively by reaction with thiourea followed by hydrolysis of the isothiouronium disalt.

They may also be prepared by reaction of a thiolactone of formula 11 with an aminothiol of formula 5, in an aprotic solvent, according to the reaction:

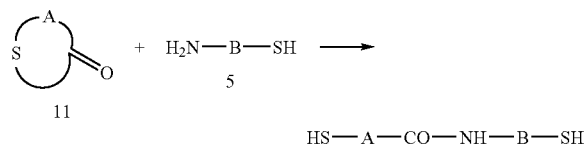

Finally, they may be prepared by a process comprising the reaction of a mercaptoamide of formula HS-A-CO—$NH_2$ with an aminothiol salt of formula HX, $H_2N$—B—SH, wherein X is chosen from chlorine and bromine atoms, at a temperature ranging from 60° C. and 200° C.

In the processes for preparation described above, A and B have the same meaning as the groups A and B in formula (II) defined above.

By way of non-limiting example, the novel dimercaptoamides of formula (II), as disclosed herein, can be prepared by the processes described below:

Process 1

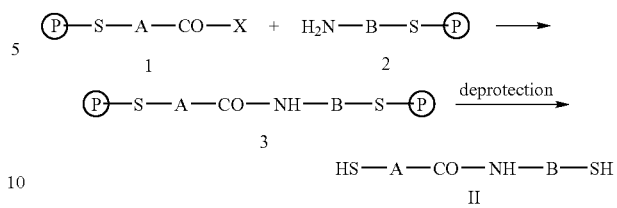

An S-protected mercapto acid halide 1 was reacted with an S-protected aminothiol 2 (Ⓟ representing a thiol function-protecting group such as, for example, a trityl, acetyl or benzyl group, and X is chosen from chlorine and bromine atoms) in an aprotic solvent such as, for example, dichloromethane, 1,2-dichloroethane, tetrahydrofuran, dimethylformamide or dioxane, in the presence of an agent intended to capture the released hydrochloric or hydrobromic acid, such as for example a tertiary amine, at a temperature ranging from 0° C. to the boiling point of the solvent.

According to a variant of Process 1, the S-protected mercapto acid halide 1 can be replaced with an S-protected mercapto acid anhydride or an S-protected mercapto ester. When an S-protected mercapto ester is used, the reaction may also be carried out in a protic solvent, for instance, an aliphatic alcohol as defined in Process 3 below.

The S-protected dimercaptoamide 3 is then deprotected to a dimercaptoamide (II), either by hydrolysis or by reduction according to the nature of the protected group Ⓟ.

Process 2

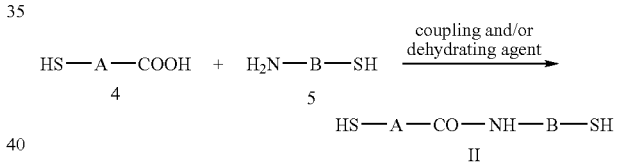

A mercapto acid 4 is reacted directly with an aminothiol 5 in the presence of a coupling and/or dehydrating agent, such as those used for peptide synthesis, for example dicyclohexylcarbodiimide or carbonyldiimidazole, in an aprotic solvent such as dichloromethane, 1,2-dichloroethane, tetrahydrofuran, dimethylformamide or dioxane, at a temperature ranging from −5° C. to 40° C.

Process 3

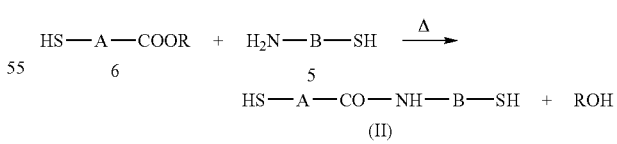

A mercapto ester 6, R being a methyl or ethyl radical, is reacted with an aminothiol 5 in the presence, optionally, of an aprotic or protic solvent, such as for example a linear or branched $C_1$-$C_5$ aliphatic alcohol, at a temperature ranging from 30° C. to 180° C. For example, the alcohol ROH formed during the reaction can be eliminated by distillation. Also, for instance, the solvent of the reaction can be an aliphatic alcohol as defined above, such as methanol.

Process 4

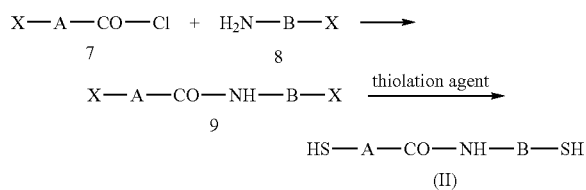

A halogenated acid halide 7 is reacted with a haloamine 8, with X being chosen from chlorine and bromine atoms, in an aprotic solvent and at a temperature and in the presence of an agent for capturing hydrochloric acid, as defined in Process 1.

In the same way as in Process 1, the halogenated acid halide 7 can be replaced with a halogenated acid anhydride or a halo ester

X—A—COOR   10

When a halo ester 10 is used, the reaction can also be carried out in a protic solvent, for example in an aliphatic alcohol as defined in Process 3.

The dihaloamide 9 obtained is converted to a dimercaptoamide (II), either by direct reaction with hydrogen sulphide in an appropriate solvent, or by reaction with thioacetic acid, for instance in salified form, followed by acid or alkaline hydrolysis of the di(S-acetyl)mercaptoamide, or alternatively by reaction with thiourea followed by hydrolysis of the isothiouronium disalt.

Process 5

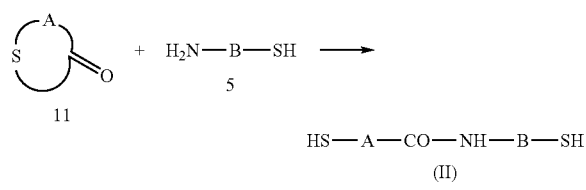

A thiolactone 11 is reacted with an aminothiol 5 in an aprotic solvent such as dichloromethane, 1,2-dichloroethane, tetrahydrofuran, diemthylformamide or dioxane, at a temperature ranging from 0° C. to the boiling point of the solvent.

Process 6

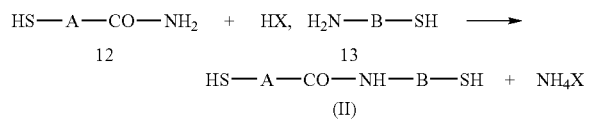

A mercaptoamide 12 is reacted with an aminothiol salt 13, wherein X is chosen from chlorine and bromine atoms, in the presence, optionally, of an inert solvent, at a temperature ranging from 60° C. to 200° C., so as to directly obtain the dimercaptoamide (II).

Depending on the nature of the substituents A and B, and on the availability of the starting materials, these various processes can also be combined by, for example, reacting a mercapto ester 6 HS-A-COOR with a haloamine 8 so as to obtain the mercaptohaloamide 14 HS-A-CO—NH—B—X, which is then converted to a dimercaptoamide (II) using a thiolation agent as defined in Process 4.

Conversely, a halo ester 10 X-A-COOR can also be reacted with an aminothiol 5 H₂N—B—SH so as to obtain the mercaptohaloamide 15 X-A-CO—NH—B—SH which is then converted to a dimercaptoamide (II) using a thiolation agent as defined above.

In the processes using an S-protected aminothiol 2, or an aminothiol 5, or a haloamine 8, these amino compounds are used either directly in the form of a base, or in salified form in the presence of an equivalent of appropriate basic agent.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The examples that follow serve to illustrate the present disclosure without, however, being limiting in nature.

EXAMPLES

Preparation Examples

Example 1

Preparation of
2-mercapto-N-(2-mercaptoethyl)acetamide

Example 1a

Preparation According to Process 2

A solution of 53.5 g of dicyclohexylcarbodiimide (0.2593 mol) in 175 ml of dichloromethane was added dropwise to a solution of 23.8 g of mercaptoacetic acid (0.2584 mol) in 250 ml of dichloromethane, and cooled to 0° C. by means of an ice bath.

The addition was carried out in such a way as to keep the temperature below 5° C.

A white precipitate formed during the addition. Once the addition was complete, the reaction medium was kept at 0° C. for 2 hours under an inert (argon) atmosphere.

A suspension of 20 g of cysteamine (0.2592 mol) in 75 ml of dichloromethane was then added in a single step, and the mixture was then kept stirring for a further 12 hours at ambient temperature under an inert argon atmosphere.

After filtration through sintered glass (removal of the dicyclohexylurea), the filtrate was evaporated to dryness under reduced pressure, and then taken up with 100 ml of acetone and again filtered and then evaporated under reduced pressure.

The oil obtained was purified on a silica filter in dichloromethane.

After evaporation and drying, 30 g of 2-mercapto-N-(2-mercaptoethyl)acetamide were obtained in the form of a colorless oil.

The assaying of SH by iodometry indicated a 98% titre.

The 1H NMR spectrum at 400 Mhz (CDCl$_3$), the 13C NMR spectrum at 100 Mhz (CDCl$_3$), and also the mass spectrum were in accordance with the expected structure.

Example 1b

Preparation According to Process 3

10.6 g (0.1 mol) of methyl thioglycolate were added to a solution of 7.8 g (0.1 mol) of cysteamine in 100 cm$^3$ of methanol, maintained under argon. The mixture was then refluxed, with stirring, for 2 h, and then the methanol was distilled under normal pressure over 30 min or so.

The mixture was then heated to 85° C. and then the final traces of methanol were distilled under reduced pressure. 13.2 g of translucent oil were thus obtained. The oil was purified by silica column chromatography in dichloromethane.

After evaporation to dryness and prolonged drying, 12 g of 2-mercapto-N-(2-mercaptoethyl)acetamide were obtained in the form of a colorless oil.

The assaying of SH by iodometry indicated a 98.2% titre.

$^1$H NMR spectrum at 400 MHz (CDCl$_3$) and the $^{13}$C NMR spectrum at 100 MHz (CDCl$_3$) were in accordance with the expected structure.

Example 2

Preparation of
3-mercapto-N-(2-mercaptoethyl)propionamide

A solution of 19.36 g (0.0938 mol) of N,N'-dicyclohexylcarbodiimide in 60 cm$^3$ of dichloromethane was added dropwise to a solution of 9.92 g (0.093 mol) of 3-mercaptopropionic acid in 100 cm$^3$ of dichloromethane, maintained under argon and cooled to a temperature ranging from 0° C. to 5° C. via an ice bath.

After stirring for 1 h, a suspension of 7.3 g (0.094 mol) of cysteamine in 50 cm$^3$ of dichloromethane was then added in one go.

The stirring was maintained overnight under an argon atmosphere, allowing the mixture to return to ambient temperature. The dicyclohexylurea precipitate was separated by filtration through sintered glass. The filtrate was evaporated to dryness under reduced pressure. The solid obtained was purified by silica column chromatography in dichloromethane, gradually increasing the polarity with methanol.

After evaporation to dryness under reduced pressure and drying, 12 g of 3-mercapto-N-(2-mercaptoethyl)propionamide were obtained in the form of a white solid having a melting point of 40° C.

The assaying of SH by iodometry indicated a 98.6% titre.

The $^1$H NMR spectrum at 400 MHz (CDCl$_3$), the $^{13}$C NMR spectrum at 100 MHz (CDCl$_3$), and also the mass spectrum were in accordance with the expected structure.

Example 3

Preparation of
2-mercapto-N-(2-mercaptoethyl)propionamide

A solution of 4.5 g (0.0218 mol) of N,N'-dicyclohexylcarbodiimide in 30 cm$^3$ of dichloromethane was added dropwise to a solution of 2.3 g (0.0216 mol) of thiolactic acid in 50 cm$^3$ of dichloromethane, maintained under argon and cooled to a temperature ranging from 0° C. to 5° C. with an ice bath. The stirring was maintained for 1 h at a temperature below 10° C.

A suspension of 1.67 g (0.0216 mol) of cysteamine in 20 cm$^3$ of dichloromethane was then added. The stirring was maintained for 4 h, allowing the mixture to return to ambient temperature. The dicyclohexylurea precipitate was separated by filtration through sintered glass and the filtrate was evaporated to dryness under reduced pressure.

The solid obtained was purified by silica column chromatography in dichloromethane, gradually increasing the polarity with methanol.

After evaporation to dryness under reduced pressure and drying, 2.8 g of 2-mercapto-N-(2-mercaptoethyl) propionamide were obtained in the form of a white solid having a melting point of 53° C.

The assaying of SH by iodometry indicated a 98.8% titre.

The $^1$H NMR spectrum at 400 MHz (CDCl$_3$), the $^{13}$C NMR spectrum at 100 MHz (CDCl$_3$), and also the mass spectrum were in accordance with the expected structure.

Example 4

Preparation of N-(mercaptoacetyl)-L-cysteine a) S-tritylthioglycolic Acid 15.5 g (0.059 mol) of triphenylmethanol and then, dropwise, 6 cm$^3$ of boron trifluoride etherate were added to a solution of 5 g (0.054 mol) of thioglycolic acid in 100 cm$^3$ of acetic acid, stirred under argon. The stirring was maintained for 48 h at ambient temperature under argon.

The reaction medium was poured into 1 liter of water. The precipitate obtained was filter-dried through sintered glass, washed with an aqueous sodium bicarbonate solution until the washing water reached a neutral pH, and then once with water, and dried under vacuum at 50° C.

17 g of S-tritylthioglycolic acid were thus obtained in the form of a white solid having a melting point of 163.4° C.

The $^1$H NMR spectrum at 400 MHz (DMSO) and the $^{13}$C NMR spectrum at 100 MHz (DMSO) were in accordance with the expected structure.

b) 3-mercaptotrityl-2-(2-mercaptotritylacetylamino) propionic acid 2.5 g of N,N'-dicyclohexylcarbodiimide were added to a solution of 5 g (0.015 mol) of S-tritylthioglycolic acid obtained above in 80 cm$^3$ of N,N-dimethylformamide, and cooled to a temperature ranging from 0° C. to 5° C. with an ice bath.

The stirring was maintained for 1 h and then a suspension of 5.2 g (0.016 mol) of S-tritylcysteamine in 80 cm$^3$ of N,N-dimethylformamide was added. The stirring was maintained for 16 h, allowing the mixture to return to ambient temperature.

The reaction mixture was poured into 1 liter of water acidified with HCl. The precipitate formed was filter-dried through sintered glass and thoroughly washed with water until a neutral pH was obtained.

After drying under vacuum at 45° C., 9.7 g of 3-mercaptotrityl-2-(2-mercaptotritylacetylamino)propionic acid were obtained in the form of a white solid having a melting point of 208° C.

The $^1$H NMR spectrum at 400 MHz (CD$_3$CN) and the $^{13}$C NMR spectrum at 100 MHz (CD$_3$CN) were in accordance with the expected structure.

b) N-mercaptoacetyl-L-cysteine 125 cm$^3$ of trifluoroacetic acid and then 7.5 g (0.065 mol) of triethylsilane were added dropwise, while keeping the temperature below 10° C., to a solution of 9.7 g (0.029 mol) of 3-mercaptotrityl-2-(2-mercaptotritylacetylamino)propionic acid obtained above in 250 cm$^3$ of dichloromethane, maintained under argon and cooled to 0° C.

After stirring for 1 h, the reaction medium was evaporated to dryness under reduced pressure. The crude solid obtained was taken up with 100 cm$^3$ of ethanol. The suspension was filtered through sintered glass and the filtrate was evaporated to dryness under reduced pressure and then taken up again with 30 cm$^3$ of ethyl acetate. The insoluble material was separated by filtration through sintered glass and the filtrate was evaporated to dryness under reduced pressure.

After drying, 1.3 g of N-mercaptoacetyl-L-cysteine were obtained in the form of a white solid having a melting point of 121° C.

The $^1$H NMR spectrum at 400 MHz (DMSO), the $^{13}$C NMR spectrum at 100 MHz (DMSO) and also the mass spectrum were in accordance with the expected structure.

Composition Examples

Example 5

A reducing composition for permanently reshaping the hair was prepared by mixing the following ingredients:

| | |
|---|---|
| 2-mercapto-N-(2-mercaptoethyl)acetamide | 12.1 g |
| 20% aqueous ammonia | qs pH 8.5 |
| demineralized water | qs 100 g |

This composition was applied to wet hair that had been rolled beforehand on setting rollers. The composition was allowed to act for 15 minutes, and then the entire combination was dried with a hairdryer for 5 minutes and then rinsed thoroughly with water. The following oxidizing composition was then applied:

| | |
|---|---|
| aqueous hydrogen peroxide at 200 volumes | 4.8 g |
| citric acid | qs pH 3 |
| demineralized water | qs 100 g |

The oxidizing composition was allowed to act for 5 minutes, followed by thorough rinsing with water. The curlers were removed and the hair was dried under a hood. Beautiful vigorous curls that hold were obtained.

Example 6

A reducing composition for permanently reshaping the hair was prepared by mixing the following ingredients:

| | |
|---|---|
| 2-mercapto-N-(2-mercaptoethyl)acetamide | 12.1 g |
| 20% aqueous ammonia | qs pH 7.0 |
| demineralized water | qs 100 g |

This composition was applied to wet hair that had been rolled beforehand on setting rollers. The composition was allowed to act for 15 minutes, then the entire combination was dried with a hairdryer for 5 minutes and the hair was rinsed thoroughly with water. The following oxidizing composition was then applied:

| | |
|---|---|
| aqueous hydrogen peroxide at 200 volumes | 4.8 g |
| citric acid | qs pH 3 |
| demineralized water | qs 100 g |

The oxidizing composition was allowed to act for 5 minutes, followed by thorough rinsing with water. The curlers were removed and the hair was dried under a hood. Beautiful vigorous curls that hold were obtained.

Example 7

A reducing composition for permanently reshaping the hair was prepared according to the present disclosure by mixing the following ingredients:

| | |
|---|---|
| 3-mercapto-N-(2-mercaptoethyl)propionamide | 8.3 g |
| 20% aqueous ammonia | qs pH 7.1 |
| demineralized water | qs 100 g |

This composition was applied to wet hair that had been rolled beforehand on setting rollers. After having allowed the composition to act for 20 minutes, the entire combination was dried with a hairdryer for 5 minutes and then the hair was thoroughly rinsed with water. The following oxidizing composition was then applied:

| | |
|---|---|
| aqueous hydrogen peroxide at 200 volumes | 4.8 g |
| citric acid | qs pH 3 |
| demineralized water | qs 100 g |

The oxidizing composition was allowed to act for 5 minutes, followed by thorough rinsing with water. The curlers were removed and the hair was dried under a hood. Beautiful vigorous curls that hold were obtained.

Example 8

A reducing composition for permanently reshaping the hair was prepared according to the present disclosure by mixing the following ingredients:

| | |
|---|---|
| 2-mercapto-N-(2-mercaptoethyl)propionamide | 8.3 g |
| 20% aqueous ammonia | qs pH 7.2 |
| demineralized water | qs 100 g |

This composition was applied to wet hair that had been rolled beforehand on setting rollers. After having allowed the composition to act for 25 minutes, the entire combination was dried with a hairdryer for 5 minutes and then the hair was thoroughly rinsed with water. The following oxidizing composition was then applied:

| | |
|---|---|
| aqueous hydrogen peroxide at 200 volumes | 4.8 g |
| citric acid | qs pH 3 |
| demineralized water | qs 100 g |

The oxidizing composition was allowed to act for 5 minutes, followed by thorough rinsing with water. The curlers were removed and the hair was dried under a hood. Beautiful vigorous curls that hold were obtained.

Example 9

A reducing composition for permanently reshaping the hair was prepared according to the present disclosure by mixing the following ingredients:

| | |
|---|---|
| N-mercaptoacetyl-L-cysteine | 18.83 g |
| 20% aqueous ammonia | qs pH 7.0 |
| demineralized water | qs 100 g |

This composition was applied to wet hair that had been rolled beforehand on setting rollers. After having allowed the composition to act for 25 minutes, the entire combination was dried with a hairdryer for 5 minutes and then the hair was thoroughly rinsed with water. The following oxidizing composition was then applied:

| | |
|---|---|
| aqueous hydrogen peroxide at 200 volumes | 4.8 g |
| citric acid | qs pH 3 |
| demineralized water | qs 100 g |

The oxidizing composition was allowed to act for 5 minutes, followed by thorough rinsing with water. The curlers were removed and the hair was dried under a hood. Beautiful vigorous curls that hold were obtained.

What is claimed is:

1. A process for perming keratin fibers, comprising applying, to the fibers, a reducing composition, and then an oxidizing composition, wherein the reducing composition comprises, as a reducing agent, at least one dimercaptoamide of formula (I) and the organic and inorganic salts thereof:

$$HS-A-CO-NH-B-SH \quad (I)$$

wherein:
A is chosen from $(CH_2)_n$ radicals, with n being an integer ranging from 1 to 5, optionally substituted with:
(i) at least one radical chosen from linear and branched $C_1$-$C_5$ alkyl radicals; phenyl; benzyl; amino; acetylamino; NH—CO—CH$_2$—NH$_2$, NH—CO—CH$_2$—CH$_2$—CH(NH$_2$)COOH, NH—CO—CH$_2$—CH$_2$—CH(COOH)COOH; CH$_2$—COON; CH$_2$—COOCH$_3$, and CH$_2$—COOCH$_2$—CH$_3$ radicals, or
(ii) two methyl radicals or two ethyl radicals,
and B is chosen from $(CH_2)_p$ radicals, with p being an integer ranging from 1 to 5, optionally substituted with:
(i) at least one radical chosen from linear and branched $C_1$-$C_5$ alkyl radicals; carboxyl; COOCH$_3$, COOEt; CONH$_2$; CONH—CH$_3$; CON(CH$_3$)$_2$; CONH—CH$_2$—CH$_3$, CON(CH$_2$—CH$_3$)$_2$; CONH—CH$_2$—CHOH—CH$_3$; CO—NH—CH(COOH)—(CH$_2$)$_4$—NH$_2$; CO—NH—CH(COOH)—(CH$_2$)$_4$—N(CH$_3$)$_2$; CO—NH—CH$_2$—CH$_2$—COOEt; CO—NH—CH(COOH)-iPr; and CO—NH—CH$_2$—R radicals wherein R is chosen from CO—NH$_2$, (CH$_2$)$_3$—NH$_2$, (CH$_2$)$_4$—NH$_2$, (CH$_2$)$_5$—NH$_2$, and (CH$_2$)$_4$—OH radicals, or
(ii) 2 methyl radicals,
wherein the sum of n+p ranges from 2 to 6 wherein the at least one dimercaptoamide of formula (I) is present in an amount ranging from 0.05% to 35% by weight, relative to the total weight of the reducing composition.

2. The process according to claim 1, wherein the keratin fibers are hair.

3. The process according to claim 1, wherein the at least one dimercaptoamide of formula (I) is present in an amount ranging from 1% to 20% by weight, relative to the total weight of the reducing composition.

4. The process according to claim 1, wherein the pH of the reducing composition ranges from 4 to 11.

5. The process according to claim 4, wherein the pH of the reducing composition ranges from 6 to 10.

6. The process according to claim 1, wherein the reducing composition further comprises at least one reducing agent chosen from thioglycolic acid, thiolactic acid and their ester and amide derivatives; cysteamine and its $C_1$-$C_4$ acylated derivatives; cysteine; N-acetylcysteine; thiomalic acid; pantethein; 2,3-dimercaptosuccinic acid; alkali metal and alkaline-earth metal sulphites and bisulphites; N-(mercaptoalkyl)-ω-hydroxyalkylamides; N-mono- and N,N-dialkylmercapto-4-butyramides; aminomercaptoalkylamides; N-(mercaptoalkyl)succinamic acid and N-(mercaptoalkyl)succinimide derivatives; alkylaminomercaptoalkylamides; the azeotropic mixture of 2-hydroxypropyl thioglycolate and of (2-hydroxy-1-methyl)ethyl thioglycolate, mercapto alkylaminoamides; N-mercaptoalkylalkanediamides; and formamidinesulphinic acid derivatives.

7. The process according to claim 1, wherein the reducing composition further comprises at least one surfactant chosen from nonionic, anionic, cationic and amphoteric surfactants.

8. The process according to claim 7, wherein the at least one surfactant is chosen from alkyl sulphates, alkylbenzene sulphates, alkyl ether sulphates, alkylsulphonates, quaternary ammonium salts, alkylbetaines, oxyethylenated alkylphenols, fatty acid alkanolamides, oxyethylenated fatty acid esters, and hydroxypropyl ethers.

9. The process according to claim 1, wherein the reducing composition further comprises at least one compound chosen from linear and cyclic, volatile and nonvolatile silicones; polydimethylsiloxanes; quaternized polyorganosiloxanes; polyorganosiloxanes comprising aminoalkyl groups modified with alkoxycarbonylalkyl groups; polydimethylsiloxanes comprising stearoxydimethicone end groups; polydimethylsiloxane-dialkylammonium acetate copolymers; polydimethylsiloxane-polyalkylbetaine copolymers; polysiloxanes organomodified with mercapto and/or mercaptoalkyl groups; and silanes.

10. The process according to claim 1, wherein the reducing composition further comprises at least one compound chosen from cationic polymers of the ionene type, basic amino acids, glutamic acid, aspartic acid, peptides and derivatives thereof, protein hydrolysates, waxes, swelling agents, penetrating agents, dimethylisosorbitol, urea and its derivatives, pyrrolidone, N-alkylpyrrolidones, thiamorpholinone, alkylene glycol alkyl ethers, dialkylene glycol alkyl ethers, $C_3$-$C_6$ alkane diols, 2-imidazolidinone, fatty alcohols, lanolin derivatives, pantothenic acid, agents for preventing hair loss, antidandruff agents, thickeners, suspending agents, sequestering agents, opacifiers, colorants, sunscreens, fragrances, preserving agents, thickeners, and gelling agents.

11. The process according to claim 1, wherein the oxidizing composition comprises at least one oxidizing agent chosen from aqueous hydrogen peroxide, alkali metal bromates, persalts, polythionates, and mixtures of alkali metal bromates and persalts.

12. The process according to claim 1, wherein the at least one dimercaptoamide of formula (I) in the reducing composition is chosen from:
- 2-mercapto-N-(mercaptomethyl)acetamide,
- 2-mercapto-N-(2-mercaptoethyl)acetamide,
- 2-mercapto-N-(3-mercaptopropyl)acetamide,
- 2-mercapto-N-(4-mercaptobutyl)acetamide,
- 2-mercapto-N-(5-mercaptopentyl)acetamide,
- 3-mercapto-2-(2-mercaptoacetylamino)propionamide,
- 3-mercapto-2-(2-mercaptoacetylamino)-N,N-dimethylpropionamide,
- 2-mercapto-N-(2-mercapto-1,1-dimethylethyl)acetamide,
- 2-mercapto-N-(1-mercaptomethylpropyl)acetamide,
- ethyl mercapto[(mercaptoacetyl)amino]acetate,
- N-(mercaptoacetyl)-L-cysteine,
- N-(mercaptoacetyl)-L-homocysteine,
- N-(mercaptoacetyl)-L-homocysteine, sodium salt,
- 2-mercapto-N-mercaptomethylpropionamide,
- 2-mercapto-N-(2-mercaptoethyl)propionamide,
- 2-mercapto-N-(3-mercaptopropyl)propionamide,
- 2-mercapto-N-(4-mercaptobutyl)propionamide,
- 2-mercapto-N-(5-mercaptopentyl)propionamide,
- mercapto-[(2-mercapto-1-oxopropyl)amino]acetic acid,
- N-(2-mercapto-1-oxopropyl)-DL-cysteine,
- (R)-N-(2-mercapto-1-oxopropyl)-L-cysteine,
- (S)—N-(2-mercapto-1-oxopropyl)-L-cysteine,
- 2-mercaptopropionyl-L-cysteine,
- N-(1-carbamoyl-2-mercaptoethyl)-2-mercaptopropionamide,
- N-(1-dimethylcarbamoyl-2-mercaptoethyl)-2-mercaptopropionamide,
- 4-mercapto-2-(2-mercaptopropionylamino)butyric acid,
- 2-mercapto-N-(2-mercapto-1,1-dimethylethyl)propionamide,
- 2-mercaptobutanoic acid mercaptomethylamide,
- 2-mercaptobutanoic acid (2-mercaptoethyl)amide,
- 2-mercaptobutanoic acid (3-mercaptopropyl)amide,
- 2-mercaptobutanoic acid (4-mercaptobutyl)amide,
- 2-mercaptobutanoic acid (5-mercaptopentyl)amide,
- 2-mercaptobutanoic acid (1-carbamoyl-2-mercaptoethyl)amide,
- N-(1-dimethylcarbamoyl-2-mercaptoethyl)-2-mercaptobutyramide,
- 2-mercaptobutanoic acid (1-carbamoyl-3-mercaptopropyl)amide,
- 2-mercaptobutanoic acid (2-mercapto-1,1-dimethylethyl)amide,
- 2-mercaptopentanoic acid mercaptomethylamide,
- 2-mercaptopentanoic acid (2-mercaptoethyl)amide,
- 2-mercaptopentanoic acid (3-mercaptopropyl)amide,
- 2-mercaptopentanoic acid (4-mercaptobutyl)amide,
- 2-mercaptopentanoic acid (5-mercaptopentyl)amide,
- 3-mercapto-2-(2-mercaptopentanoylamino)propionic acid,
- 2-mercaptopentanoic acid (1-carbamoyl-2-mercaptoethyl)amide,
- 2-mercaptopentanoic acid (1-dimethylcarbamoyl-2-mercaptoethyl)amide,
- 2-mercaptopentanoic acid (1-carbamoyl-3-mercaptopropyl)amide,
- 2-mercaptopentanoic acid (2-mercapto-1,1-dimethylethyl)amide,
- ethyl mercapto[(mercaptophenylacetyl)amino]acetate,
- (R)-N-[2-(mercaptomethyl)-1-oxo-3-phenylpropyl]-L-cysteine,
- (R)-N-[2-(mercaptomethyl)-1-oxo-3-phenylpropyl]-L-homocysteine,
- (S)-N-[2-(mercaptomethyl)-1-oxo-3-phenylpropyl]-L-homocysteine,
- 3-mercapto-N-(2-mercaptoethyl)propanamide,
- 3-mercapto-N-mercaptomethylpropionamide,
- 3-mercapto-N-(3-mercaptopropyl)propionamide,
- 3-mercapto-N-(4-mercaptobutyl)propionamide,
- N-(3-mercapto-1-oxopropyl)-L-cysteine,
- 3-mercapto-2-(3-mercaptopropionylamino)propionamide,
- N-(1-dimethylcarbamoyl-2-mercaptoethyl)-3-mercaptopropionamide,
- 4-mercapto-2-(3-mercaptopropionylamino)butyric acid,
- 3-mercapto-N-(2-mercapto-1,1-dimethylethyl)propionamide,
- 3-mercapto-N-mercaptomethyl-2-methylpropionamide,
- 3-mercapto-N-(2-mercaptoethyl)-2-methylpropionamide,
- 3-mercapto-N-(3-mercaptopropyl)-2-methylpropionamide,
- 3-mercapto-N-(4-mercaptobutyl)-2-methylpropionamide,
- 3-mercapto-2-(3-mercapto-2-methylpropionylamino)propionic acid,
- N-(1-carbamoyl-2-mercaptoethyl)-3-mercapto-2-methylpropionamide,
- N-(1-dimethylcarbamoyl-2-mercaptoethyl)-3-mercapto-2-methylpropionamide,
- 3-mercapto-N-(2-mercapto-1,1-dimethylethyl)-2-methylpropionamide,
- N-(3-mercapto-2-methyl-1-oxopropyl)-L-homocysteine,
- N-[2-(mercaptomethyl)-1-oxo-3-phenylpropyl]cysteine,
- methyl 4-[(1-carboxy-2-mercaptoethyl)amino]-3-(mercaptomethyl)-4-oxobutanoate,
- N-mercaptomethyl-3-mercaptomethylsuccinamic acid,
- N-(2-mercaptoethyl)-3-mercaptomethylsuccinamic acid,
- N-(3-mercaptopropyl)-3-mercaptomethylsuccinamic acid,
- N-(4-mercaptobutyl)-3-mercaptomethylsuccinamic acid,
- N-(1-carboxy-2-mercaptoethyl)-3-mercaptomethylsuccinamic acid,
- N-(1-carboxy-3-mercaptopropyl)-3-mercaptomethylsuccinamic acid,
- N-(2-mercapto-1,1-dimethylethyl)-3-mercaptomethylsuccinamic acid,
- N-(2-mercapto-1-ethyl)-3-mercaptomethylsuccinamic acid,
- 2-mercapto-N-mercaptomethyl-2-methylpropionamide,
- 2-mercapto-N-(2-mercaptoethyl)-2-methylpropanamide,
- 2-mercapto-N-(3-mercaptopropyl)-2-methylpropionamide,
- 2-mercapto-N-(4-mercaptobutyl)-2-methylpropionamide,
- 2-mercapto-N-(5-mercaptopentyl)-2-methylpropionamide,
- 2-mercapto-N-(2-mercapto-1,1-dimethylethyl)-2-methylpropionamide,
- 2-mercapto-N-(2-mercapto-1-ethyl)-2-methylpropionamide,
- N-(2-mercapto-2-methyl-1-oxopropyl)-D-cysteine,
- N-(2-mercapto-2-methyl-1-oxopropyl)cysteine, N-(2-mercapto-2-methyl-1-oxopropyl)-L-cysteine, monosodium salt,
N-(2-mercapto-2-methyl-1-oxopropyl)-L-cysteine,
(R)-N-[2-amino-1-(mercaptomethyl)-2-oxoethyl]-2-mercapto-2-methylpropanamide,
methyl N-(2-mercapto-2-methyl-1-oxopropyl)-L-cysteinate,
(2R)-3-mercapto-2-[(2-mercapto-2-methyl-1-oxopropyl)amino]-N,N-dimethylpropanamide,
N2-[N-(2-mercapto-2-methyl-1-oxopropyl)-L-cysteinyl]-L-lysine,
N-(2-mercapto-2-methyl-1-oxopropyl)homocysteine,
N-(2-ethyl-2-mercapto-1-oxobutyl)-L-cysteine,
3-mercapto-N-mercaptomethyl-3-methylbutyramide,
3-mercapto-N-(2-mercaptoethyl)-3-methylbutanamide,
3-mercapto-N-(3-mercaptopropyl)-3-methylbutyramide,
3-mercapto-N-(4-mercaptobutyl)-3-methylbutyramide,
N-(3-mercapto-3-methyl-1-oxobutyl)-L-cysteine,
N-(1-carbamoyl-2-mercaptoethyl)-3-mercapto-3-methylbutyramide,
N-(1-dimethylcarbamoyl-2-mercaptoethyl)-3-mercapto-3-methylbutyramide,
4-mercapto-2-(3-mercapto-3-methylbutyrylamino)butyric acid,
3-mercapto-N-(2-mercapto-1,1-dimethylethyl)-3-methylbutyramide,
3-mercapto-N-(2-mercapto-1-ethyl)-3-methylbutyramide,
3-mercapto-N-mercaptomethyl-2,2-dimethylpropionamide,
3-mercapto-N-(2-mercaptoethyl)-2,2-dimethylpropionamide,
3-mercapto-N-(3-mercaptopropyl)-2,2-dimethylpropionamide,
3-mercapto-N-(4-mercaptobutyl)-2,2-dimethylpropionamide,
3-mercapto-N-(2-mercapto-1,1-dimethylethyl)-2,2-dimethylpropionamide,
N-(3-mercapto-2,2-dimethyl-1-oxopropyl)-D-cysteine,
N-(3-mercapto-2,2-dimethyl-1-oxopropyl)-L-cysteine,
N-(1-carbamoyl-2-mercaptoethyl)-3-mercapto-2,2-dimethylpropionamide,
N-(1-dimethylcarbamoyl-2-mercaptoethyl)-3-mercapto-2,2-dimethylpropionamide,
N-(3-mercapto-2,2-dimethyl-1-oxopropyl)-D-cysteinylglycinamide,
N6-[(1,1-dimethylethoxy)carbonyl]-N2-[N-(3-mercapto-2,2-dimethyl-1-oxopropyl)-L-cysteinyl]-L-lysine,
N-[2-[(4-aminobutyl)amino]-1-(mercaptomethyl)-2-oxoethyl]-3-mercapto-2,2-dimethylpropanamide, monohydrochloride,
N-[2-[(5-aminopentyl)amino]-1-(mercaptomethyl)-2-oxoethyl]-3-mercapto-2,2-dimethylpropanamide, monohydrochloride,
N-[2-[(6-aminohexyl)amino]-1-(mercaptomethyl)-2-oxoethyl]-3-mercapto-2,2-dimethylpropanamide, monohydrochloride,
(R)-N-[2-[(5-hydroxypentyl)amino]-1-(mercaptomethyl)-2-oxoethyl]-3-mercapto-2,2-dimethylpropanamide,
N2-[N-(3-mercapto-2,2-dimethyl-1-oxopropyl)-L-cysteinyl]-L-lysine,
N2-[N-(3-mercapto-2,2-dimethyl-1-oxopropyl)-L-cysteinyl]-N6,N6-dimethyl-L-lysine,
3-mercapto-N-(3-mercapto-2,2-dimethyl-1-oxopropyl)-D-valine,
N-(3-mercapto-2,2-dimethyl-1-oxopropyl)homocysteine,
N-[2-ethyl-2-(mercaptomethyl)-1-oxobutyl]-L-cysteine,
2-amino-3-mercapto-N-mercaptomethylpropionamide,
(2R)-2-amino-3-mercapto-N-(2-mercaptoethyl)propanamide,
(2S)-2-amino-3-mercapto-N-(2-mercaptoethyl)propanamide,
2-amino-3-mercapto-N-(3-mercaptopropyl)propionamide,
2-amino-3-mercapto-N-(4-mercaptobutyl)propionamide,
L-cysteinyl-L-cysteine,
methyl mercapto[(mercaptoacetyl)amino]acetate,
ethyl L-cysteinyl-L-cysteinate,
2-amino-N-(1-carbamoyl-2-mercaptoethyl)-3-mercaptopropionamide,
2-amino-N-(1-carbamoyl-2-mercaptoethyl)-3-mercapto-N,N-dimethylpropionamide,
2-(2-amino-3-mercaptopropionylamino)-4-mercaptobutyric acid,
2-amino-3-mercapto-N-(2-mercapto-1,1-dimethylethyl)propionamide,
2-amino-3-mercapto-N-(2-mercapto-1-ethyl)propionamide,
2-acetylamino-3-mercapto-N-mercaptomethylpropionamide,
(2R)-2-(acetylamino)-3-mercapto-N-(2-mercaptoethyl)propanamide,
2-acetylamino-3-mercapto-N-(3-mercaptopropyl)propionamide,
2-acetylamino-3-mercapto-N-(4-mercaptobutyl)propionamide,
2-(2-acetylamino-3-mercaptopropionylamino)-3-mercapto-3-methylbutyric acid,
2-acetylamino-3-mercapto-N-(1-mercaptomethylpropyl)propionamide,
2-acetylamino-N-(1-dimethylcarbamoyl-2-mercaptoethyl)-3-mercaptopropionamide,
N-acetyl-L-cysteinyl-L-cysteine,
N-(N-acetylcysteinyl)-L-cysteine,
N-(N-acetylcysteinyl)-DL-cysteine,
ethyl N-acetyl-L-cysteinyl-D-cysteinate,
ethyl N-acetyl-L-cysteinyl-L-cysteinate,
2-acetamido-N-(1-carbamoyl-2-mercaptoethyl)-3-mercaptopropionamide,
ethyl N-acetyl-L-cysteinyl-L-cysteinyl-glycinate,
2-(2-acetylamino-3-mercaptopropionylamino)-4-mercaptobutyric acid,
2-(carboxymethylamino)-3-mercapto-N-mercaptomethylpropionamide,
2-(carboxymethylamino)-3-mercapto-N-(2-mercaptoethyl)propionamide,
2-(carboxymethylamino)-3-mercapto-N-(3-mercaptopropyl)propionamide,
2-(carboxymethylamino)-3-mercapto-N-(4-mercaptobutyl)propionamide,
2-(carboxymethylamino)-N-(1-carbamoyl-2-mercaptoethyl)-3-mercaptopropionamide,
2-[2-(carboxymethylamino)-3-mercaptopropionylamino]-3-mercaptopropionic acid,
[1-(1-carbamoyl-2-mercaptoethylcarbamoyl)-2-mercaptoethylamino]acetic acid,
2-(carboxymethylamino)-3-mercapto-N-(2-mercapto-1,1-dimethylethyl)propionamide,
N-[N-[N-(carboxymethyl)-L-cysteinyl]-L-cysteinyl]-D-valine,
2-amino-4-[2-mercapto-1-(mercaptomethylcarbamoyl)ethylcarbamoyl]butyric acid, 2-amino-4-[2-mercapto-1-(2-mercaptoethylcarbamoyl)
ethylcarbamoyl]butyric acid,
2-amino-4-[2-mercapto-1-(3-mercaptopropylcarbamoyl)
ethylcarbamoyl]butyric acid,
2-amino-4-[2-mercapto-1-(4-mercaptobutylcarbamoyl)
ethylcarbamoyl]butyric acid,
L-γ-glutamyl-L-cysteinyl-L-cysteine,
2-[2-(4-amino-4-carboxybutyrylamino)-3-mercaptopropionylamino]-4-mercaptobutyric acid,
2-amino-4-[1-(1-carbamoyl-2-mercaptoethylcarbamoyl)-2-mercaptoethylcarbamoyl]butyric acid,
2-amino-4-[1-(1-dimethylcarbamoyl-2-mercaptoethylcarbamoyl)-2-mercaptoethylcarbamoyl]butyric acid,
2-amino-4-[2-mercapto-1-(2-mercapto-1,1-dimethylethylcarbamoyl)ethylcarbamoyl]butyric acid,
2-amino-4-[2-mercapto-1-(2-mercapto-1-ethylethylcarbamoyl)ethylcarbamoyl]butyric acid,
2-(2-aminoacetylamino)-3-mercapto-N-mercaptomethylpropionamide,
2-(2-aminoacetylamino)-3-mercapto-N-(2-mercaptoethyl)propionamide,
2-(2-aminoacetylamino)-3-mercapto-N-(3-mercaptopropyl)propionamide,
2-(2-aminoacetylamino)-3-mercapto-N-(4-mercaptobutyl)propionamide,
2-(2-aminoacetylamino)-3-mercapto-N-(5-mercaptopentyl)propionamide,
glycyl-L-cysteinyl-L-cysteine,
2-[2-(2-aminoacetylamino)-3-mercaptopropionylamino]-4-mercaptobutyric acid,
2-(2-aminoacetylamino)-3-mercapto-N-(2-mercapto-1,1-dimethylethyl)propionamide,
2-(2-aminoacetylamino)-3-mercapto-N-(1-mercaptomethylpropyl)propionamide,
4-carboxy-L-α-glutamyl-L-cysteinyl-L-cysteine,
(S)-N-[N-(5-amino-5-carboxy-1-oxopentyl)-L-homocysteinyl]-L-cysteine,
4-mercapto-N-mercaptomethylbutyramide,
4-mercapto-N-(2-mercaptoethyl)butyramide,
4-mercapto-N-(3-mercaptopropyl)butyramide,
N-(4-mercapto-1-oxobutyl)-L-cysteine,
4-mercapto-2-(3-mercaptopropionylamino)butyramide,
N-(1-dimethylcarbamoyl-2-mercaptoethyl)-4-mercaptobutyramide,
N-(4-mercapto-1-oxobutyl)-L-homocysteine,
4-mercapto-N-(2-mercapto-1,1-dimethylethyl)butyramide,
4-mercapto-N-(1-mercaptomethylpropyl)butyramide,
5-mercaptopentanoic acid mercaptomethylamide,
5-mercaptopentanoic acid (2-mercaptoethyl)amide,
N-(5-mercapto-1-oxopentyl)-L-cysteine,
5-mercapto-2-(3-mercaptopropionylamino)pentanamide,
N-(1-dimethylcarbamoyl-2-mercaptoethyl)-5-mercaptopentanamide,
5-mercapto-N-(2-mercapto-1,1-dimethylethyl)pentanamide,
5-mercapto-N-(1-mercaptomethylpropyl)pentanamide, and
6-mercaptohexanoic acid mercaptomethylamide.

13. The process according to claim 12, wherein the at least one dimercaptoamide of formula (I) in the reducing composition is chosen from:
2-mercapto-N-(mercaptomethyl)acetamide,
2-mercapto-N-(2-mercaptoethyl)acetamide,
2-mercapto-N-(3-mercaptopropyl)acetamide,
2-mercapto-N-(4-mercaptobutyl)acetamide,
2-mercapto-N-(5-mercaptopentyl)acetamide,
3-mercapto-2-(2-mercaptoacetylamino)propionamide,
3-mercapto-2-(2-mercaptoacetylamino)-N,N-dimethylpropionamide,
2-mercapto-N-(2-mercapto-1,1-dimethylethyl)acetamide,
2-mercapto-N-(1-mercaptomethylpropyl)acetamide,
N-(mercaptoacetyl)-L-cysteine,
N-(mercaptoacetyl)-L-homocysteine,
2-mercapto-N-mercaptomethylpropionamide,
2-mercapto-N-(2-mercaptoethyl)propionamide,
2-mercapto-N-(3-mercaptopropyl)propionamide,
2-mercapto-N-(4-mercaptobutyl)propionamide,
2-mercapto-N-(5-mercaptopentyl)propionamide,
mercapto-[(2-mercapto-1-oxopropyl)amino]acetic acid,
2-mercaptopropionyl-L-cysteine,
N-(1-carbamoyl-2-mercaptoethyl)-2-mercaptopropionamide,
N-(1-dimethylcarbamoyl-2-mercaptoethyl)-2-mercaptopropionamide,
4-mercapto-2-(2-mercaptopropionylamino)butyric acid,
2-mercapto-N-(2-mercapto-1,1-dimethylethyl)propionamide,
2-mercaptobutanoic acid mercaptomethylamide,
2-mercaptobutanoic acid (2-mercaptoethyl)amide,
2-mercaptobutanoic acid (3-mercaptopropyl)amide,
2-mercaptobutanoic acid (4-mercaptobutyl)amide,
2-mercaptopentanoic acid mercaptomethylamide,
2-mercaptopentanoic acid (2-mercaptoethyl)amide,
2-mercaptopentanoic acid (3-mercaptopropyl)amide,
3-mercapto-N-(2-mercaptoethyl)propanamide,
3-mercapto-N-mercaptomethylpropionamide,
3-mercapto-N-(3-mercaptopropyl)propionamide,
3-mercapto-N-(4-mercaptobutyl)propionamide,
N-(3-mercapto-1-oxopropyl)-L-cysteine,
3-mercapto-2-(3-mercaptopropionylamino)propionamide,
N-(1-dimethylcarbamoyl-2-mercaptoethyl)-3-mercaptopropionamide,
4-mercapto-2-(3-mercaptopropionylamino)butyric acid,
3-mercapto-N-(2-mercapto-1,1-dimethylethyl)propionamide,
3-mercapto-N-mercaptomethyl-2-methylpropionamide,
3-mercapto-N-(2-mercaptoethyl)-2-methylpropionamide,
3-mercapto-N-(3-mercaptopropyl)-2-methylpropionamide,
3-mercapto-N-(4-mercaptobutyl)-2-methylpropionamide,
3-mercapto-2-(3-mercapto-2-methylpropionylamino)propionic acid,
N-(1-carbamoyl-2-mercaptoethyl)-3-mercapto-2-methylpropionamide,
N-(1-dimethylcarbamoyl-2-mercaptoethyl)-3-mercapto-2-methylpropionamide,
3-mercapto-N-(2-mercapto-1,1-dimethylethyl)-2-methylpropionamide,
N-(3-mercapto-2-methyl-1-oxopropyl)-L-homocysteine,
N-mercaptomethyl-3-mercaptomethylsuccinamic acid,
N-(2-mercaptoethyl)-3-mercaptomethylsuccinamic acid,
N-(3-mercaptopropyl)-3-mercaptomethylsuccinamic acid,
N-(4-mercaptobutyl)-3-mercaptomethylsuccinamic acid,
N-(1-carboxy-2-mercaptoethyl)-3-mercaptomethylsuccinamic acid,
2-mercapto-N-mercaptomethyl-2-methylpropionamide,
2-mercapto-N-(2-mercaptoethyl)-2-methylpropanamide,
2-mercapto-N-(3-mercaptopropyl)-2-methylpropionamide,
2-mercapto-N-(4-mercaptobutyl)-2-methylpropionamide, 2-mercapto-N-(2-mercapto-1,1-dimethylethyl)-2-methyl-propionamide,
2-mercapto-N-(2-mercapto-1-ethyl)-2-methylpropionamide,
N-(2-mercapto-2-methyl-1-oxopropyl)-L-cysteine,
N-(2-ethyl-2-mercapto-1-oxobutyl)-L-cysteine,
3-mercapto-N-mercaptomethyl-3-methylbutyramide,
3-mercapto-N-(2-mercaptoethyl)-3-methylbutanamide,
3-mercapto-N-(3-mercaptopropyl)-3-methylbutyramide,
N-(3-mercapto-3-methyl-1-oxobutyl)-L-cysteine,
N-(1-carbamoyl-2-mercaptoethyl)-3-mercapto-3-methylbutyramide,
N-(1-dimethylcarbamoyl-2-mercaptoethyl)-3-mercapto-3-methylbutyramide,
4-mercapto-2-(3-mercapto-3-methylbutyrylamino)butyric acid,
3-mercapto-N-mercaptomethyl-2,2-dimethylpropionamide,
3-mercapto-N-(2-mercaptoethyl)-2,2-dimethylpropionamide,
3-mercapto-N-(3-mercaptopropyl)-2,2-dimethylpropionamide,
3-mercapto-N-(4-mercaptobutyl)-2,2-dimethylpropionamide,
N-(3-mercapto-2,2-dimethyl-1-oxopropyl)-L-cysteine,
N-(1-carbamoyl-2-mercaptoethyl)-3-mercapto-2,2-dimethylpropionamide,
N-(1-dimethylcarbamoyl-2-mercaptoethyl)-3-mercapto-2,2-dimethylpropionamide,
N-[2-ethyl-2-(mercaptomethyl)-1-oxobutyl]-L-cysteine,
2-amino-3-mercapto-N-mercaptomethylpropionamide,
(2R)-2-amino-3-mercapto-N-(2-mercaptoethyl)propanamide,
(2S)-2-amino-3-mercapto-N-(2-mercaptoethyl)propanamide,
2-amino-3-mercapto-N-(3-mercaptopropyl)propionamide,
2-amino-3-mercapto-N-(4-mercaptobutyl)propionamide,
L-cysteinyl-L-cysteine,
2-amino-N-(1-carbamoyl-2-mercaptoethyl)-3-mercaptopropionamide,
2-amino-N-(1-carbamoyl-2-mercaptoethyl)-3-mercapto-N,N-dimethylpropionamide,
2-(2-amino-3-mercaptopropionylamino)-4-mercaptobutyric acid,
2-amino-3-mercapto-N-(2-mercapto-1,1-dimethylethyl)propionamide,
2-amino-3-mercapto-N-(2-mercapto-1-ethyl)propionamide,
2-acetylamino-3-mercapto-N-mercaptomethylpropionamide,
N-acetyl-L-cysteinyl-L-cysteine,
2-(carboxymethylamino)-3-mercapto-N-mercaptomethylpropionamide,
2-(carboxymethylamino)-3-mercapto-N-(2-mercaptoethyl)propionamide,
2-(carboxymethylamino)-3-mercapto-N-(3-mercaptopropyl)propionamide,
L-γ-glutamyl-L-cysteinyl-L-cysteine,
2-(2-aminoacetylamino)-3-mercapto-N-mercaptomethylpropionamide,
2-(2-aminoacetylamino)-3-mercapto-N-(2-mercaptoethyl)propionamide,
glycyl-L-cysteinyl-L-cysteine,
4-carboxy-L-α-glutamyl-L-cysteinyl-L-cysteine,
4-mercapto-N-mercaptomethylbutyramide,
4-mercapto-N-(2-mercaptoethyl)butyramide,
4-mercapto-N-(3-mercaptopropyl)butyramide,
N-(4-mercapto-1-oxobutyl)-L-cysteine,
4-mercapto-2-(3-mercaptopropionylamino)butyramide,
N-(1-dimethylcarbamoyl-2-mercaptoethyl)-4-mercaptobutyramide,
4-mercapto-N-(2-mercapto-1,1-dimethylethyl)butyramide,
4-mercapto-N-(1-mercaptomethylpropyl)butyramide,
5-mercaptopentanoic acid mercaptomethylamide,
5-mercaptopentanoic acid (2-mercaptoethyl)amide,
N-(5-mercapto-1-oxopentyl)-L-cysteine,
5-mercapto-2-(3-mercaptopropionylamino)pentanamide,
N-(1-dimethylcarbamoyl-2-mercaptoethyl)-5-mercaptopentanamide,
5-mercapto-N-(2-mercapto-1,1-dimethylethyl)pentanamide,
5-mercapto-N-(1-mercaptomethylpropyl)pentanamide, and
6-mercaptohexanoic acid mercaptomethylamide.

14. A kit for perming the hair, comprising
at least one first compartment comprising a reducing composition comprising at least one reducing agent chosen from dimercaptoamides of formula (I) and the organic and inorganic salts thereof:

$$HS-A-CO-NH-B-SH \quad (I)$$

wherein:
A is chosen from $(CH_2)_n$ radicals, with n being an integer ranging from 1 to 5, optionally substituted with:
(i) at least one radical chosen from linear and branched $C_1$-$C_5$ alkyl radicals; and phenyl; benzyl; amino; acetylamino; $NH-CO-CH_2-NH_2$; $NH-CO-CH_2-CH_2-CH(NH_2)COOH$; $NH-CO-CH_2-CH_2-CH(COOH)COOH$; $CH_2-COOH$; $CH_2-COOCH_3$; and $CH_2-COOCH_2-CH_3$ radicals, or
(ii) two methyl radicals or two ethyl radicals,
and B is chosen from $(CH_2)_p$ radicals, with p being an integer ranging from 1 to 5, optionally substituted with:
(i) at least one radical chosen from linear and branched $C_1$-$C_5$ alkyl radicals; and carboxyl; $COOCH_3$; COOEt; $CONH_2$; $CONH-CH_3$; $CON(CH_3)_2$; $CONH-CH_2-CH_3$; $CON(CH_2-CH_3)_2$; $CONH-CH_2-CHOH-CH_3$; $CO-NH-CH(COOH)-(CH_2)_4-NH_2$; $CO-NH-CH(COOH)-(CH_2)_4-N(CH_3)_2$; $CO-NH-CH_2-CH_2-COOEt$; $CO-NH-CH(COOH)$-iPr; and $CO-NH-CH_2-R$ radicals wherein R is chosen from $CO-NH_2$, $(CH_2)_3-NH_2$, $(CH_2)_4-NH_2$, $(CH_2)_5-NH_2$, and $(CH_2)_4-OH$ radicals, or
(ii) 2 methyl radicals,
wherein the sum of n+p ranges from 2 to 6 wherein the at least one dimercaptoamide of formula (I) is present in an amount ranging from 0.05% to 35% by weight, relative to the total weight of the reducing composition; and
at least one second compartment comprising at least one oxidizing composition.

* * * * *

UNITED STATES PATENT AND TRADEMARK OFFICE
CERTIFICATE OF CORRECTION

PATENT NO. : 7,875,268 B2  
APPLICATION NO. : 11/099585  
DATED : January 25, 2011  
INVENTOR(S) : Michel Philippe et al.

Page 1 of 1

It is certified that error appears in the above-identified patent and that said Letters Patent is hereby corrected as shown below:

In claim 1, column 29, line 58, "NH-CO-CH$_2$-NH$_2$," should read --NH-CO-CH$_2$-NH$_2$;--.

In claim 1, column 29, lines 58-59, "NH-CO-CH$_2$-CH$_2$-CH(NH$_2$)COOH," should read --NH-CO-CH$_2$-CH$_2$-CH(NH$_2$)COOH;--.

In claim 1, column 29, line 60, "CH$_2$-COON;" should read --CH$_2$-COOH;--.

In claim 1, column 29, lines 60-61, "CH$_2$-COOCH$_3$," should read --CH$_2$-COOCH$_3$;--.

In claim 1, column 29, line 66, "COOCH$_3$," should read --COOCH$_3$;--.

In claim 1, column 29, line 67-column 30, line 1, "CONH-CH$_2$-CH$_3$," should read --CONH-CH$_2$-CH$_3$;--.

Signed and Sealed this  
Third Day of May, 2011

David J. Kappos  
*Director of the United States Patent and Trademark Office*